(12) United States Patent
Lie

(10) Patent No.: US 11,564,786 B2
(45) Date of Patent: Jan. 31, 2023

(54) VASCULAR FILTER SYSTEM AND METHOD OF DEPLOYMENT AND RETRIEVAL OF A VASCULAR FILTER

(71) Applicant: Kevin T. Lie, Greenville, DE (US)

(72) Inventor: Kevin T. Lie, Greenville, DE (US)

(*) Notice: Subject to any disclaimer, the term of this patent is extended or adjusted under 35 U.S.C. 154(b) by 359 days.

(21) Appl. No.: 16/708,407

(22) Filed: Dec. 9, 2019

(65) Prior Publication Data

US 2020/0107922 A1    Apr. 9, 2020

Related U.S. Application Data

(63) Continuation-in-part of application No. 15/747,641, filed as application No. PCT/US2017/041625 on Jul. 12, 2017, now Pat. No. 10,500,034.

(60) Provisional application No. 62/491,867, filed on Apr. 28, 2017.

(51) Int. Cl.
*A61F 2/01* (2006.01)

(52) U.S. Cl.
CPC .......... *A61F 2/0105* (2020.05); *A61F 2/011* (2020.05); *A61F 2210/0004* (2013.01); *A61F 2210/0014* (2013.01); *A61F 2220/0016* (2013.01); *A61F 2250/0098* (2013.01)

(58) Field of Classification Search
CPC .......... A61F 2/0105; A61F 2/01; A61F 2/011; A61F 2210/0014; A61F 2250/0098; A61F 2220/0016; A61F 2210/0004; A61F 2/0103; A61F 2/012; A61F 2/013; A61F 2/014; A61F 2002/016; A61F 2002/018
See application file for complete search history.

(56) References Cited

U.S. PATENT DOCUMENTS

| 5,350,398 A | 9/1994 | Pavcnik et al. |
| 5,779,716 A | 7/1998 | Cano et al. |
| 6,217,600 B1 * | 4/2001 | DiMatteo .............. A61F 2/0105 606/198 |
| 8,562,638 B2 | 10/2013 | Sokolov et al. |

(Continued)

FOREIGN PATENT DOCUMENTS

WO    WO 01-08595 A1    2/2001

OTHER PUBLICATIONS

Supplemental European Search Report for EP 17907334.

*Primary Examiner* — Kathleen S Holwerda
*Assistant Examiner* — Uyen N Vo
(74) *Attorney, Agent, or Firm* — Devlin Law Firm LLC; James M. Lennon

(57) ABSTRACT

A vascular filter system for deploying a vascular filter utilizes a plurality of tensors that extend radially outward from a deployment sheath. The ends of the tensors are coupled with an attachment ring of the vascular filter and a plurality of attachment barbs are coupled with the attachment ring for securing the filter to the vessel wall. A method for retrieving the vascular filter from the vessel utilizes a reverse curve catheter, a guidewire that extends therethrough and an intravascular snare. The guidewire is advanced around the filter and into the snare which secures the guidewire around the filter for retrieval. A vessel distention device utilizes one or more distention tensors having a distention feature on the extended end, such as a blunt tip, to press on the inside vessel wall. The distention tensors extend out radially from a sheath to press on the vessel wall.

19 Claims, 27 Drawing Sheets

(56) References Cited

U.S. PATENT DOCUMENTS

| | | | |
|---|---|---|---|
| 2006/0015136 A1* | 1/2006 | Besselink | A61F 2/01 606/200 |
| 2006/0095068 A1* | 5/2006 | WasDyke | A61F 2/0105 606/200 |
| 2008/0027481 A1 | 1/2008 | Gilson et al. | |
| 2009/0005803 A1* | 1/2009 | Batiste | A61F 2/0105 606/200 |
| 2010/0016881 A1 | 1/2010 | Fleck et al. | |
| 2010/0030253 A1 | 2/2010 | Harris et al. | |
| 2012/0022580 A1* | 1/2012 | McCartney | A61B 17/221 606/200 |
| 2012/0221040 A1* | 8/2012 | Eggers | A61F 2/0105 606/200 |
| 2013/0226222 A1 | 8/2013 | Eggers | |
| 2015/0173884 A1* | 6/2015 | Johnson | A61F 2/0103 606/200 |
| 2016/0038271 A1* | 2/2016 | Johnsen | A61F 2/01 606/200 |

\* cited by examiner

VASCULAR FILTER SYSTEM AND METHOD OF DEPLOYMENT AND RETRIEVAL OF A VASCULAR FILTER

CROSS REFERENCE TO RELATED APPLICATIONS

The present application is a continuation-in-part of U.S. patent application Ser. No. 15/747,641, filed on Jan. 25, 2018, entitled Vascular Filter System and Method of Deployment and Retrieval of Vascular Filter, which is a National Stage Application of International Patent Application No. PCT/US2017/041625, filed on Jul. 12, 2017, entitled Vascular Filter System and Method of Deployment and Retrieval of a Vascular Filter, which claims the benefit of priority to U.S. Provisional Patent Application No. 62/491,867, filed on Apr. 28, 2017, entitled Intravascular Web and Delivery Device System and Method.

BACKGROUND OF THE INVENTION

Field of the Invention

The invention relates to a vascular filter system and method to deploy and retrieve the vascular filter.

Background

Vascular filters are used to prevent emboli and other debris from flowing to critical areas of the body, such as the brain or lungs. Vascular filters are often deployed but are seldom retrieved. In many cases, the vascular filter is retained in the vessel was with barbs. These bars can extend through the vessel wall leading to leakage from the vessel and/or damage to surrounding tissue. Most vascular filters comprise wire frames and/or wire filter elements. These wires can fracture due to flex fatigue and flow downstream along the vessel and lodge in undesirable locations. In addition, the vascular filter can slide along the vessel and may block branch vessels in doing so, or flow to undesirable locations. Finally, vascular filters can occlude over time which may lead to thrombus formation. There is some description of vascular filters that comprise bioresorbable materials in the prior art, however these devices comprise wire frame components that require removal.

SUMMARY OF THE INVENTION

The invention is directed to a vascular filter system for deploying a vascular filter and a system and method for retrieving the vascular filter from a lumen, such as a vessel. An exemplary vascular filter comprises an attachment ring, a plurality of attachment barbs coupled to the attachment ring, and a plurality of filter strand threads forming a vascular filter web portion having filter openings. The vascular filter portion is coupled to the attachment ring and a plurality of attachment barbs extend from the attachment ring for attaching and retaining the vascular filter to a lumen. In an exemplary embodiment, the filter strands comprise, consist essentially of or consist of a bioresorbable material. In an exemplary embodiment, the filter strand threads are very flexible and non-free-standing, as defined herein. The filter web may be flexible and easily deformable, like a net. The filter web may have filter opening that are no more than about 10 mm, or no more than about 8 mm, or no more than about 6 mm, or between 3 mm and 6 mm and any range between and including the filter opening dimensions provided. The filter opening dimension is the largest straight-line dimension across a filter opening. In an exemplary embodiment, the attachment ring and the filter web are made of bioresorbable material and the attachment barbs are made of a metallic material.

An exemplary filter web comprises ring strands and fill strands. Exemplary fill strands extend from the attachment ring, up over the distal end of the filter web and back to the attachment ring on an opposing side of the attachment ring. Exemplary ring strands extend substantially perpendicularly to the fill strands in a circle and offset an offset distance from the attachment ring. Adjacent ring strands and adjacent fill strands form filter openings. The entire filter web may be made from material that is bioresorbable. The size or composition of the filter strand threads may change from one location to another to allow a portion of the filter web to dissolve before another portion of the filter web. For example, a filter web may be designed such that the distal end, or end furthest from the attachment frame, dissolves prior to a portion of the filter web more proximal to the attachment ring. In this way, the size of particles, or portion of the filter web that may break free from the retained filter web or attachment ring may be minimized. The ring strands may be configured to dissolve prior to the fill strands, or ring strands furthest from the attachment ring may dissolve more quickly than ring strands more proximal to the attachment ring. Likewise, the fill strands may have a change in diameter or thickness wherein the fill strands are thickest or slowest to dissolve proximal to the attachment ring.

An exemplary filter portion comprises a spirographic loop that may be made up of a single continuous filter strand. This type of filter web may enable an intravascular snare to couple with and withdraw the filter web from a single location, as the filter web is made of a continuous loop. A spirographic loop type filter web may be configured with filter end loops and the attachment barbs may be connected to these filter end loops.

Fluoroscopy may be used to view the location of the vascular filter in a vessel lumen and a radiopaque material may be incorporated into the vascular filter for this purpose. The attachment barbs and/or the attachment ring may be made out of a radiopaque material or may comprise a radiopaque coating. Likewise, the filter strand threads may be made out of a radiopaque material or comprise a radiopaque coating. A radiopaque material may be gold, or platinum or other metallic material.

An exemplary vascular filter may be deployed using a vascular filter system comprising a deployment sheath that retains a plurality of tensors. The tensors may be made out of shape memory material, such as Nitinol, or out of a material have some elasticity, such as spring-metal or polymer. The tensors are retained within the deployment sheath and when the distal end of the tensor extends from the distal-end opening of the deployment sheath, they bend out radially. A tensor coupler is configured on the distal end of the tensor and the tensor coupler is coupled with the attachment ring. The vascular filter is deployed and attached to the inside wall of the vessel when the tensors extend out radially and press the attachment barbs into the vessel wall. The attachment barbs are attached to the attachment ring.

A distension device comprises a plurality of tensors that extend radially outward from an opening in a sheath and may have a distension end that is blunt for pressing on the inside vessel wall to distend it outward.

A vascular filter may be retrieved using an exemplary vascular filter retrieval system comprising a sheath, a reverse curve catheter, a guidewire and an intravascular snare. In an exemplary vascular filter retrieval method, a sheath is advanced into a vessel lumen until the distal end and sheath opening is proximal to the vascular filter that is attached to the vessel. The guidewire is then advanced through the sheath and beyond a portion of the vascular filter. The reverse curve catheter is then advanced over the guidewire and advance beyond a portion of the vascular filter, wherein the curve portion of the reverse curve catheter is beyond a portion of the vascular filter, and in some cases on the opposing side of the vascular filter from the distal end of the sheath. The guidewire is advanced through the curve portion of the reverse curve catheter and back toward the distal end of the sheath. An intravascular snare is advanced out of the sheath opening. The distal end of the guidewire is advanced through snare opening and the snare is closed to retain the guidewire therein. A loop is made around the vascular filter or a portion of the vascular filter by the reverse curve catheter and the guidewire. The guidewire and reverse curve catheter are then pulled back into the sheath to retrieve the vascular filter. A portion or all of the vascular filter may be pulled into the sheath. The distal ends of the guidewire, the reverse curve catheter and the vascular filter may be pulled into the sheath and the sheath may be withdrawn from the vessel.

In an exemplary embodiment, a tensor may be a distention tensor and have a distention feature at the extended end of the distention tensor for pressing against the inside surface of a vessel wall to distend the vessel. An exemplary distention feature may be a blunt end of the tensor or a disc shaped feature for pressing against the inside vessel wall. A distention feature may have a dimension that is at least three or five or more times greater than the diameter or cross-length dimension of the distention tensor. A distention feature may be disc, having a diameter or blunt dimension that is five or more times greater than the diameter of the distention tensor. In an exemplary embodiment, a distention device comprises two or more, or three or more distention tensors that extend out from the sheath radially in a substantially uniformly spaced circumferential orientation to distend the vessel, thereby increasing interior area or inner diameter of the vessel. A larger number of distention tensors may provide for more complete and uniform distention of the vessel, wherein a tensor extends out radially with a circumferential spacing from an adjacent distention of no more than about 130 degrees, or no more than about 120 degrees, or no more than about 90 degrees, or no more than about 60 degrees, or no more than about 45 degrees. A distention device having four distention tensors circumferentially spaced at about 90 degrees may effectively distend a vessel. A substantially uniformly spaced circumferential orientation of the distention tensors means that each tensor is space circumferentially from an adjacent tensor within about 20% of a uniform circumferential spacing, or 360 degrees divided by the number of tensors. For example, a distention device with four tensors would have a uniform spacing of 90 degrees between tensors, and a substantially uniform spacing within about 20% of 90 degrees for each adjacent tensor.

An exemplary tensor may be configured with a stylet extending through a conduit of the tensor and connected to a release feature coupled to the tensor coupler 90. An exemplary tensor coupler may be detachably attached to barb tether, which may be the attachment ring. Manipulation of the stylet, such as pulling on the stylet may release the tensor coupler from the attachment ring. A release feature on the tensor coupler may comprise a hinge, including a living hinge, to allow the coupler to detach from the barb tether. In an exemplary embodiment, the tensor coupler comprises a coupler slot that is configured around the barb tether and pulling of the stylet opens the coupler slot to disengage the tensor coupler from the barb tether. In another embodiment, the tensor coupler is retained by the barb release feature configured on the barb or on the barb tether, and manipulation of the stylet releases the tensor coupler from the barb release feature. For example, the barb release feature may extend at least partially around the tensor coupler and pulling of the stylet may release the tensor coupler from the barb release feature. In an exemplary embodiment, a vascular filter, or portion thereof is coated with a therapeutic agent including, but not limited to, heparin and paclitaxel. A therapeutic agent may prevent thrombosis.

The summary of the invention is provided as a general introduction to some of the embodiments of the invention and is not intended to be limiting. Additional example embodiments including variations and alternative configurations of the invention are provided herein.

BRIEF DESCRIPTION OF THE SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

In FIG. 21 the tensor coupler is configured around the attachment ring, and in FIG. 22 the stylet has been pulled to release the tensor coupler from the attachment ring.

In FIG. 23 the tensor coupler is coupled to a barb tether, and in FIG. 24 the stylet has been pulled to release the tensor coupler from the barb tether.

In FIG. 25 the tensor coupler is coupled to a barb tether, and in FIG. 26 the stylet has been pulled to release the tensor coupler from the barb tether.

Figure 1:
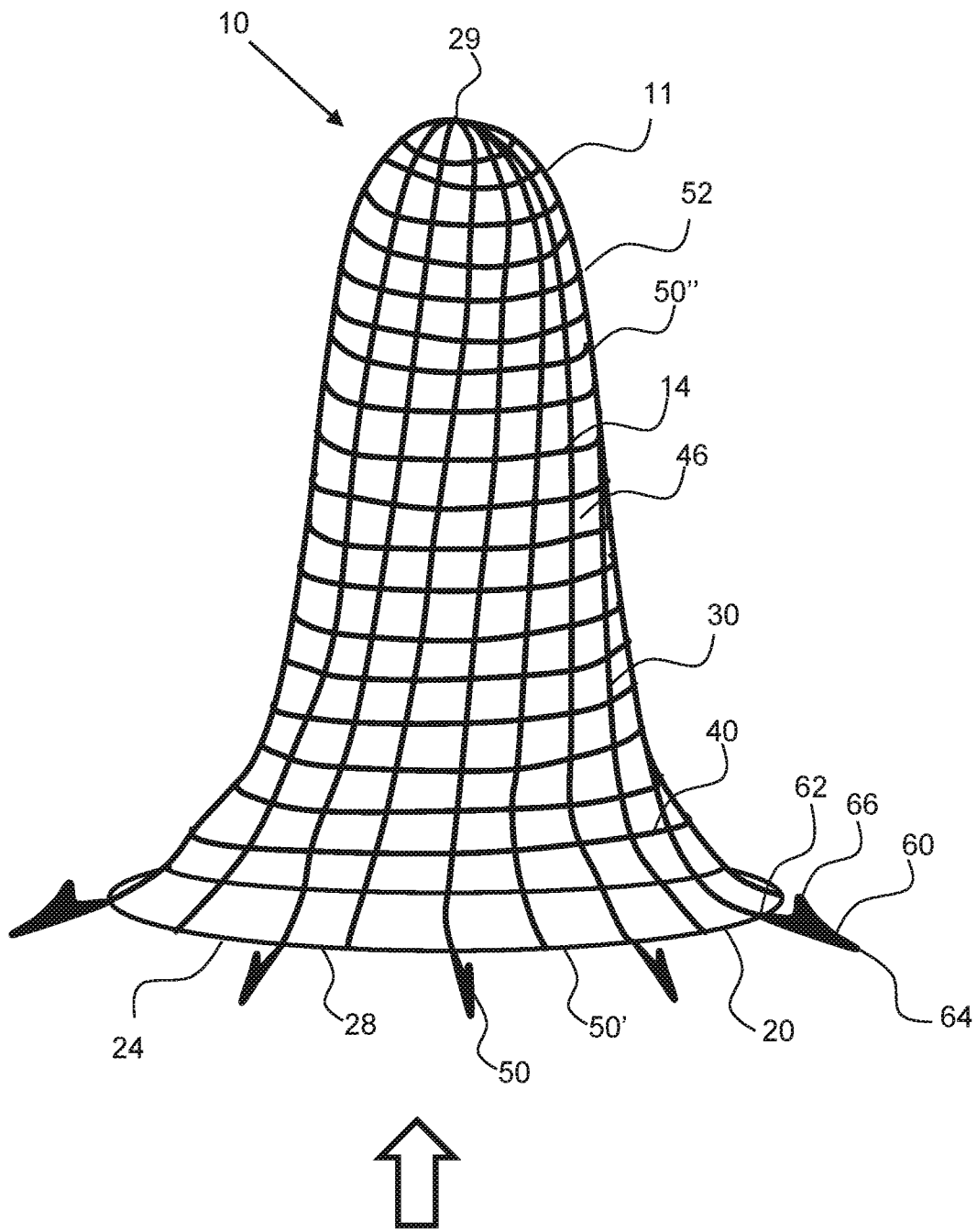
FIG. 1 shows an exemplary vascular filter comprising a filter portion an attachment ring and a plurality of attachment barbs coupled to the attachment ring.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Definitions

The filter strand threads that form the vascular filter web of the present invention are non-freestanding and flexible with little to no elastic memory. A strand thread will easily deform under a load.

As shown in FIG. 1, an exemplary vascular filter 10 comprises a filter portion 11 comprises of ring strands 40 and fill strands 30 that form a filter web 14 or mesh having openings 49 to allow for the flow of blood therethrough. The openings of the filter portion may have a maximum opening dimension, ring or fill opening dimension of no more than about 10 mm and may between 3 and 6 mm. The ring opening dimension 47 is the distance between adjacent ring strands that form an opening, and the fill opening dimension 48 is the distance between adjacent fill strands that form an opening. An attachment ring 20 is configured on the proximal end 28 of the vascular filter and a plurality of attachment barbs 60 are coupled to the attachment ring. The attachment ring is configured for placement in an upstream location relative to blood flow to the distal end 29 of the vascular filter 10. The blood flow direction is indicated by the large bold arrow. The attachment barbs are configured to penetrate into a vessel wall to retain the vascular filter to the vessel wall. The barbs have a connected end 62 proximal to the attachment ring, an insert end 64 that is sharp for insertion into vessel wall and a barb portion 66 for preventing the attachment barb from pulling out from the vessel wall. The flow of blood will cause the distal end 29 to move downstream of the proximal end 28 after attachment to a vessel wall. As shown the ring strands 40 most proximal to the attachment ring are larger in diameter than the attachment rings more proximal to the distal end 29 of the vascular filter. The vascular filter has a tapering shape from the attached or proximal end 28 to the distal end 29. The ring and fill strands may be made out of a bioresorbable material 52 that dissolves or is absorbed by the body over time. The attachment ring 20 may also be made out of a bioresorbable material. The entire filter portion 11 may be a bioresorbable material 52. The attachment barbs may be made out of metal, such as gold, and may remain in the vessel wall after the filter portion 11 is absorbed. A vascular filter 10 may have a plurality of attachment barbs configured around the circumference of the attachment ring 20 including but not limited to about three or more, about four or more, about five or more, about 8 or more, about 10 or more and any range between and including the number of attachment barbs listed. The attachment barbs may be made out of a radiopaque material or have a radiopaque material coating 50 thereon. Likewise, the attachment ring 20 may be made out of a radiopaque material or have a radiopaque material coating 50' thereon. The ring and fill strands may also comprise a radiopaque material coating 50" that will break up and be distributed into the blood flow as the strands are absorbed.

Figure 2:
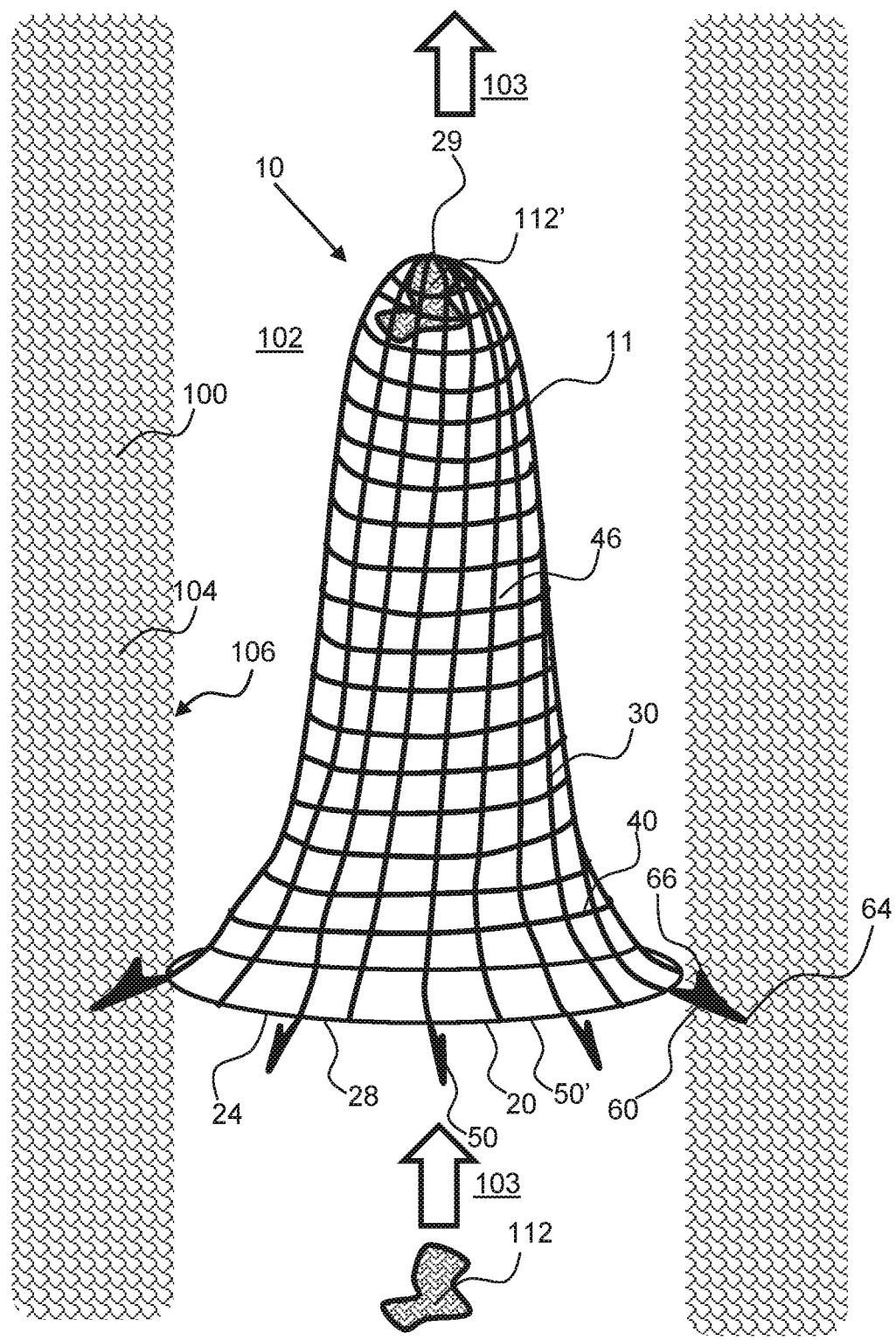
FIG. 2 shows an exemplary vascular filter attached within a vessel with the attachment barbs retained in the vessel wall.

As shown in FIG. 2, an exemplary vascular filter 10 is attached within a vessel 100 with the attachment barbs retained in the vessel wall 104. The vascular filter is retained within the vessel lumen 102 with the proximal end 28, or attached end upstream of the distal end 29, relative to blood flow. A blood clot 112, an example of a type of debris that the vascular filter may capture is shown in the blood flow 103. The blood clot is shown retained within the vascular filter 10 at the closed and distal end 29. The blood clot entered the vascular filter through the proximal end 28, or open end of the vascular filter 10. The attachment barbs 60 are shown being retained in the vessel wall 104. The insert end 64 of the attachment barb 60 has penetrated into the inside wall surface 106 and the barb portion 66 is within the vessel wall. The openings 46 of the filter portion 11 in the filter web 14, that are formed by the ring and fill strands are smaller than the blood clot 112' and therefore prevents the blood clot from flowing with the blood flow through the filter.

Figure 3:
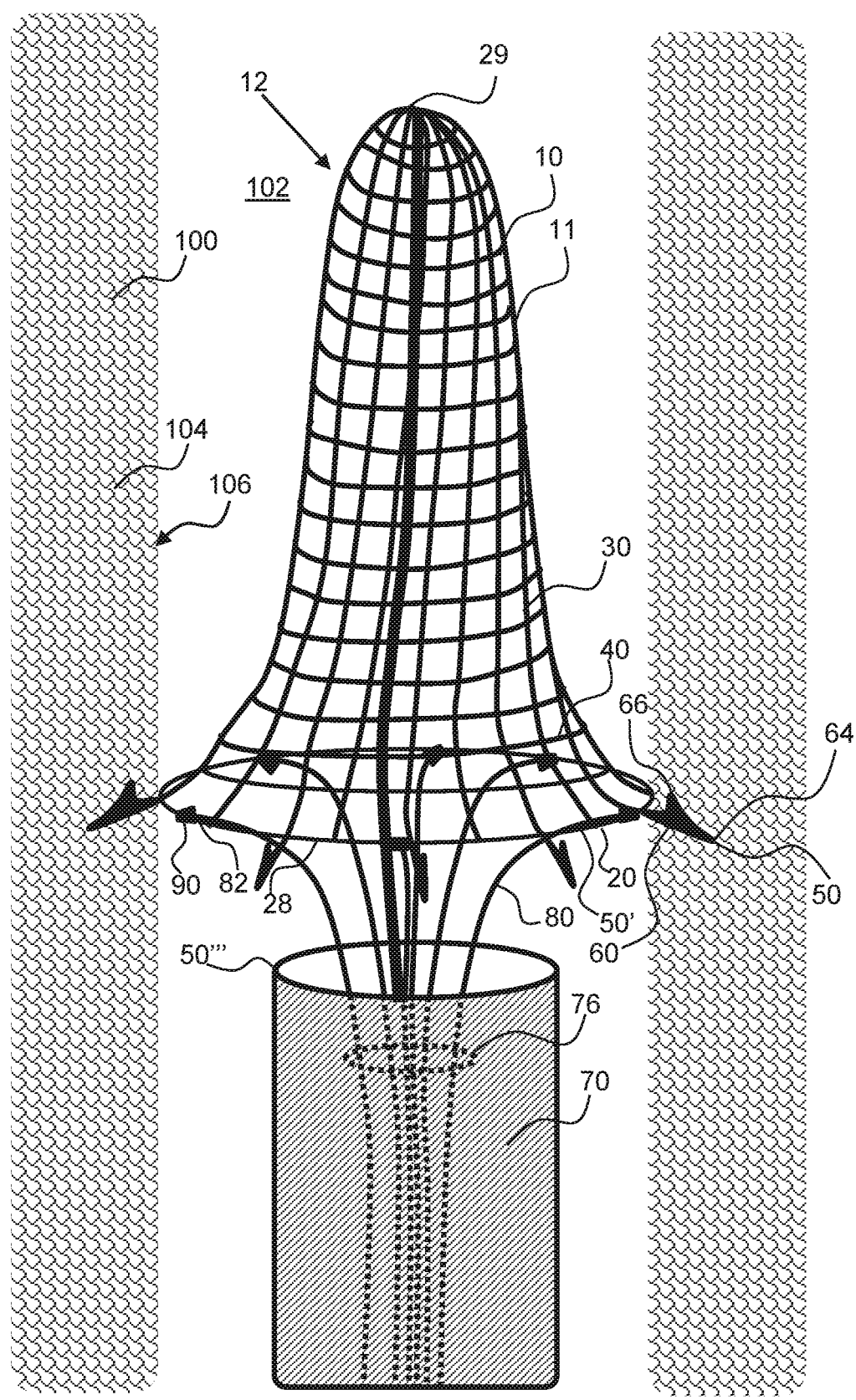
FIG. 3 shows an exemplary vascular filter system comprising a vascular filter and a deployment sheath having a plurality of tensors that extend out from the opening of the deployment sheath to expand the attachment ring to the inner vessel wall and insert the attachment barbs into the vessel wall.

As shown in FIG. 3, an exemplary vascular filter system 12 comprising an exemplary vascular filter 10 that is being deployed from a deployment sheath 70. A guide wire may be inserted into the vascular system and a deployment sheath may be fed along the guide wire to a desired location. Fluoroscopy may be used to determine when the distal end 72 of the deployment sheath is in the proper location. A radiopaque material 50, 50', 50''' may be on the attachment barb 60, the attachment ring 20 and/or the distal end 72 of the deployment sheath. In addition, radiopaque material may also be on the tensors 80 or the filtration portion 11, of the vascular filter 10. The tensors 80 are extending from the distal end opening 73 of the deployment sheath and are extending radially outward toward the interior wall surface 106 of the vessel wall 105. The tensors may have shape memory and when moved from the deployment sheath where they are retained may bend outward in a radial direction as shown and expand the attachment ring 20 to the inside wall surface 106. The attachment barbs 60 may be inserted into the vessel wall by the force exerted by the tensors. The tensor couplers 90 may drive the attachment ring and/or attachment barbs outward and thereby cause the attachment barbs to puncture the vessel wall and be retained therein. After the attachment barbs are retained in the vessel wall, the tensors may be retrieved back into the deployment sheath and the deployment sheath may be retracted from the body; leaving the vascular filter retained within the vessel lumen 102.

Figure 4:
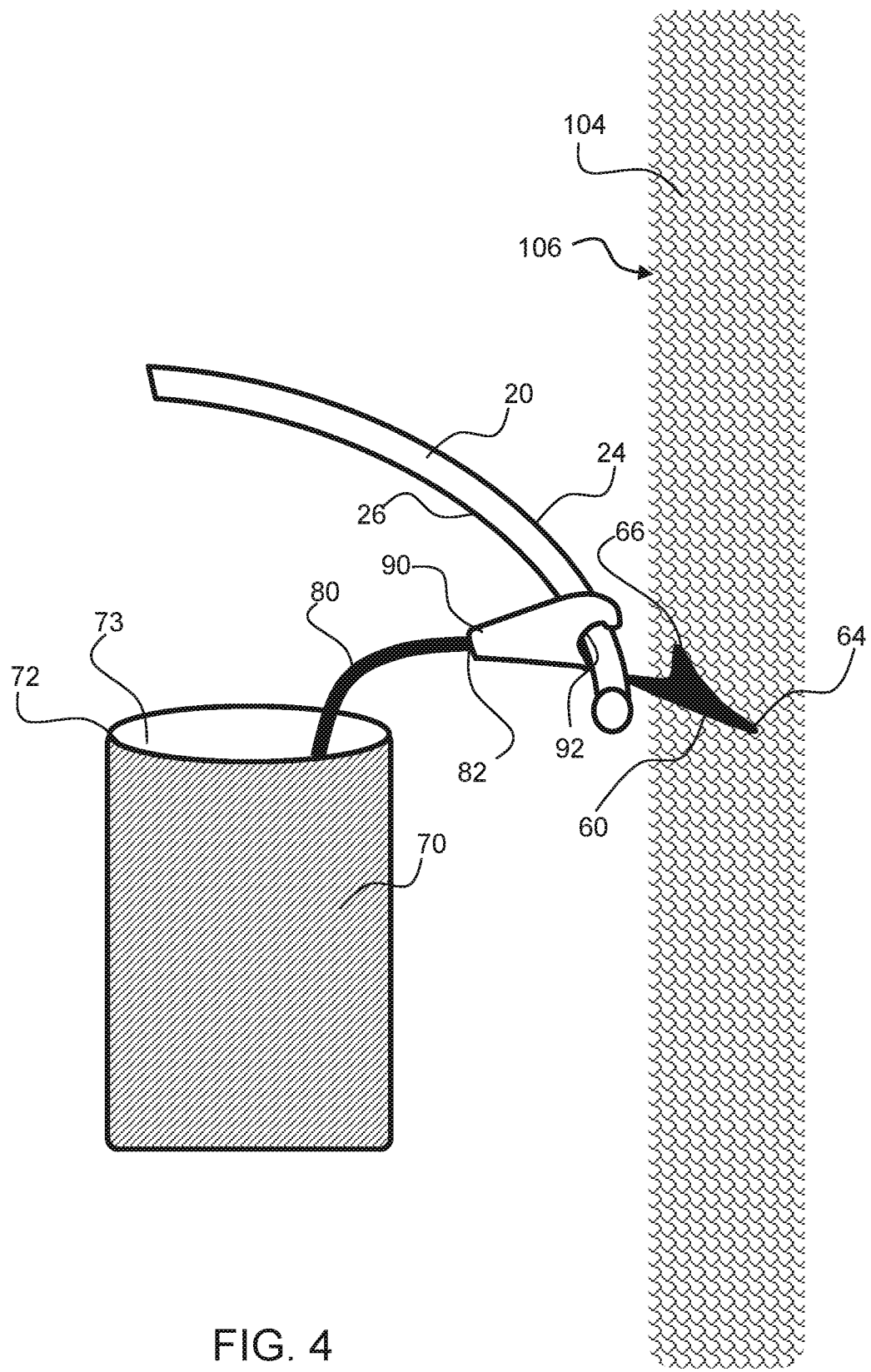
FIG. 4 shows an expanded view of a tensor extending from the opening of the deployment sheath to insert the attachment barb into the vessel wall.

As shown in FIG. 4, a tensor 80 is extending from the distal end opening 73 of the deployment sheath 70 in a radial direction and is driving the attachment ring 20 and the attachment barb 60 toward the inside wall surface 106 of the vessel wall 104. The insert end 64 of the attachment barb has pierced the vessel wall 104 and the attachment barb is driving into the vessel wall. The barb portion 66 of the attachment barb is embedded in the vessel wall to prevent the attachment barb from being withdrawn from the vessel wall. The tensor coupler 90, located at the extended end 82 of the tensor 80 couples the attachment ring 20 to the tensor. The tensor coupler has a coupler slot 92 for receiving and temporarily retaining the attachment ring or attachment barb. The coupler slot 92 receives the inside surface 26 of the attachment ring 20 and extends partially around the attachment ring perimeter. A portion of the tensor coupler may extend over to the outside surface 24 of the attachment ring.

Figure 5:
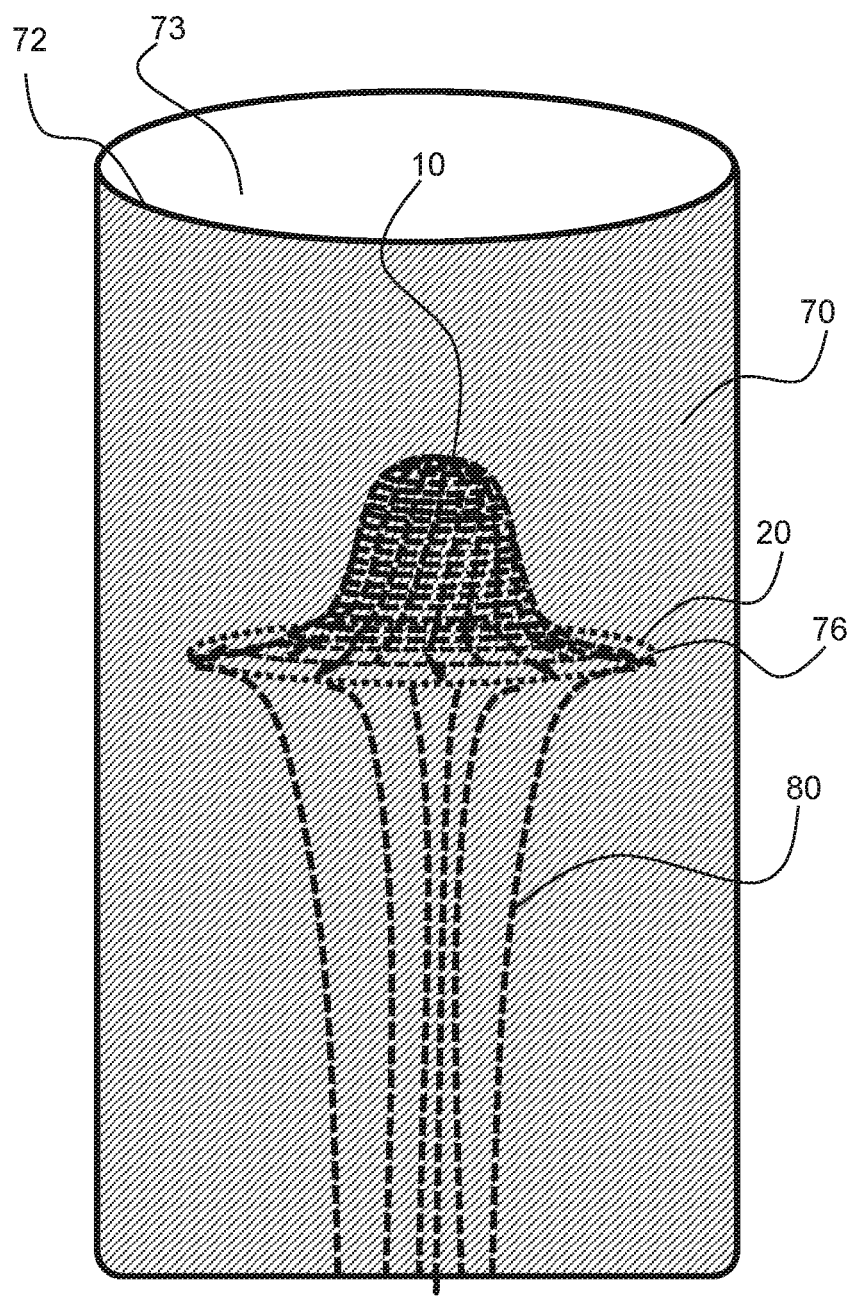
FIG. 5 shows an exemplary vascular filter system having the vascular filter coupled to a retainer ring within the deployment sheath prior to deployment.

As shown in FIG. 5, an exemplary vascular filter system 12 has the vascular filter 10 coupled to a retainer ring 76 within the deployment sheath 70 prior to deployment. The retainer ring and vascular filter may be traversed out of the distal end opening and the tensors may be pushed to extend from the retainer ring and radially expand to attach the vascular filter to the vessel wall.

Figure 6:
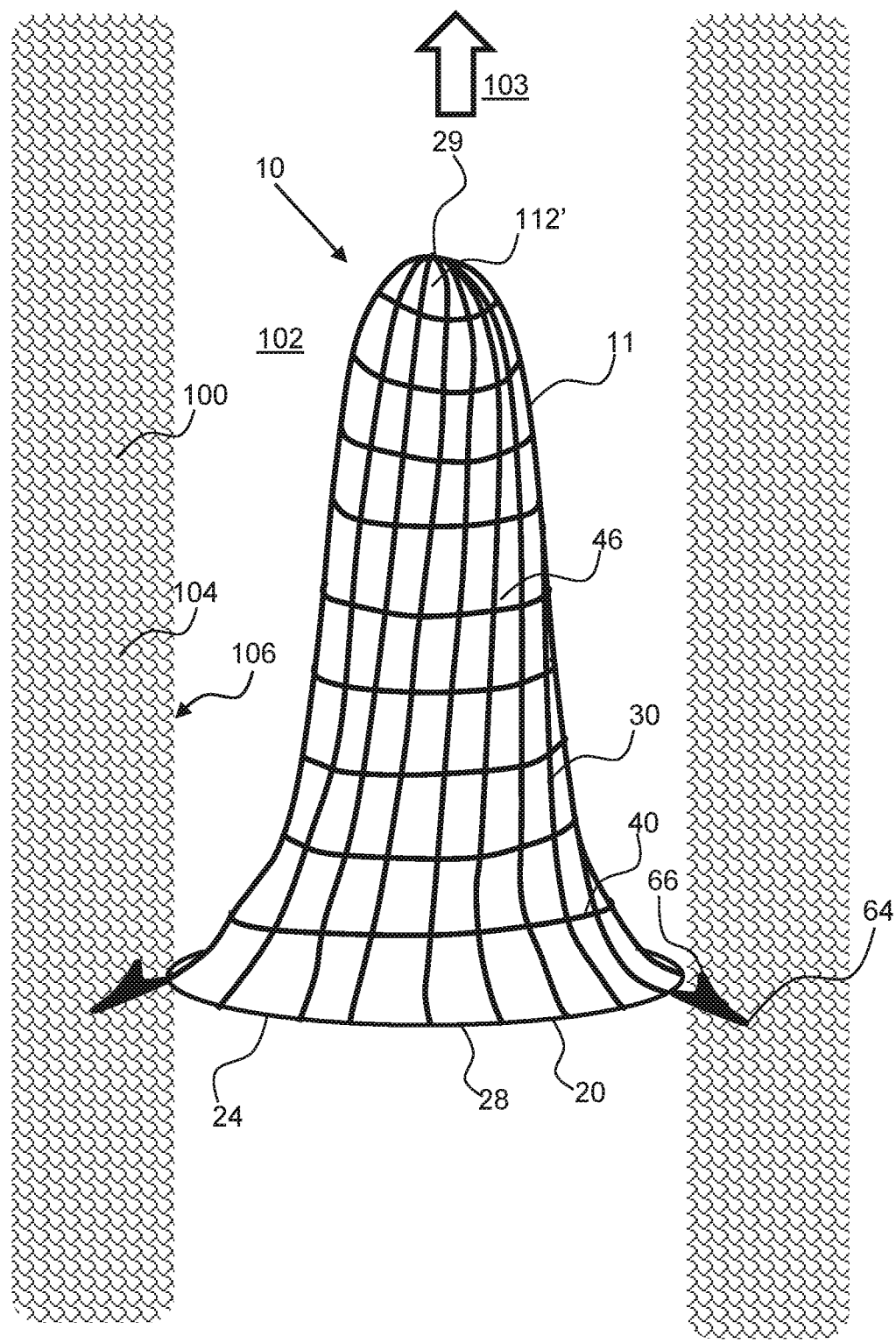
FIGS. 6 to 10 show exemplary progressive decomposition of the vascular filter 10, wherein portions of the vascular filter portion dissolve more quickly than other portions.
Figure 7:
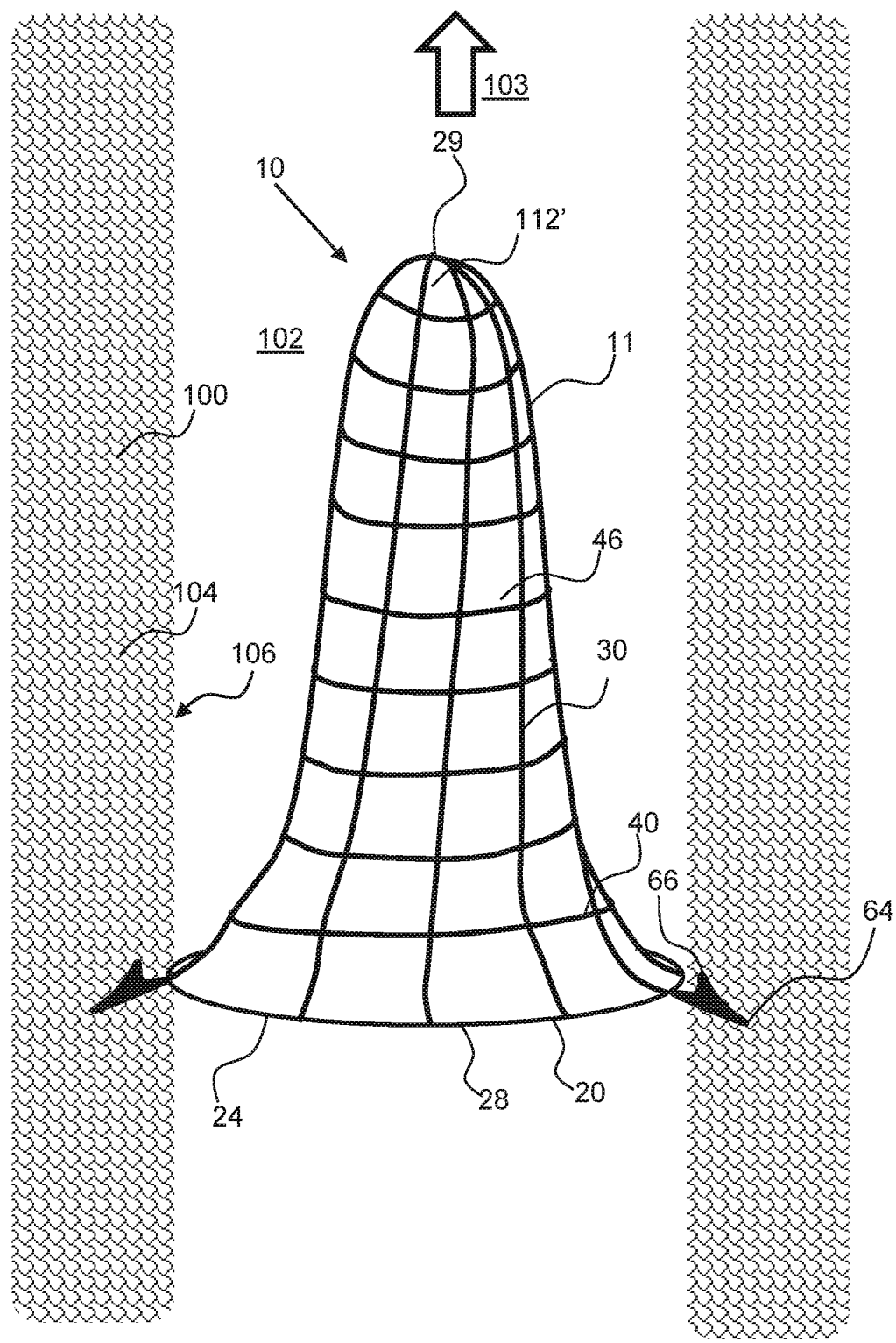
Figure 8:
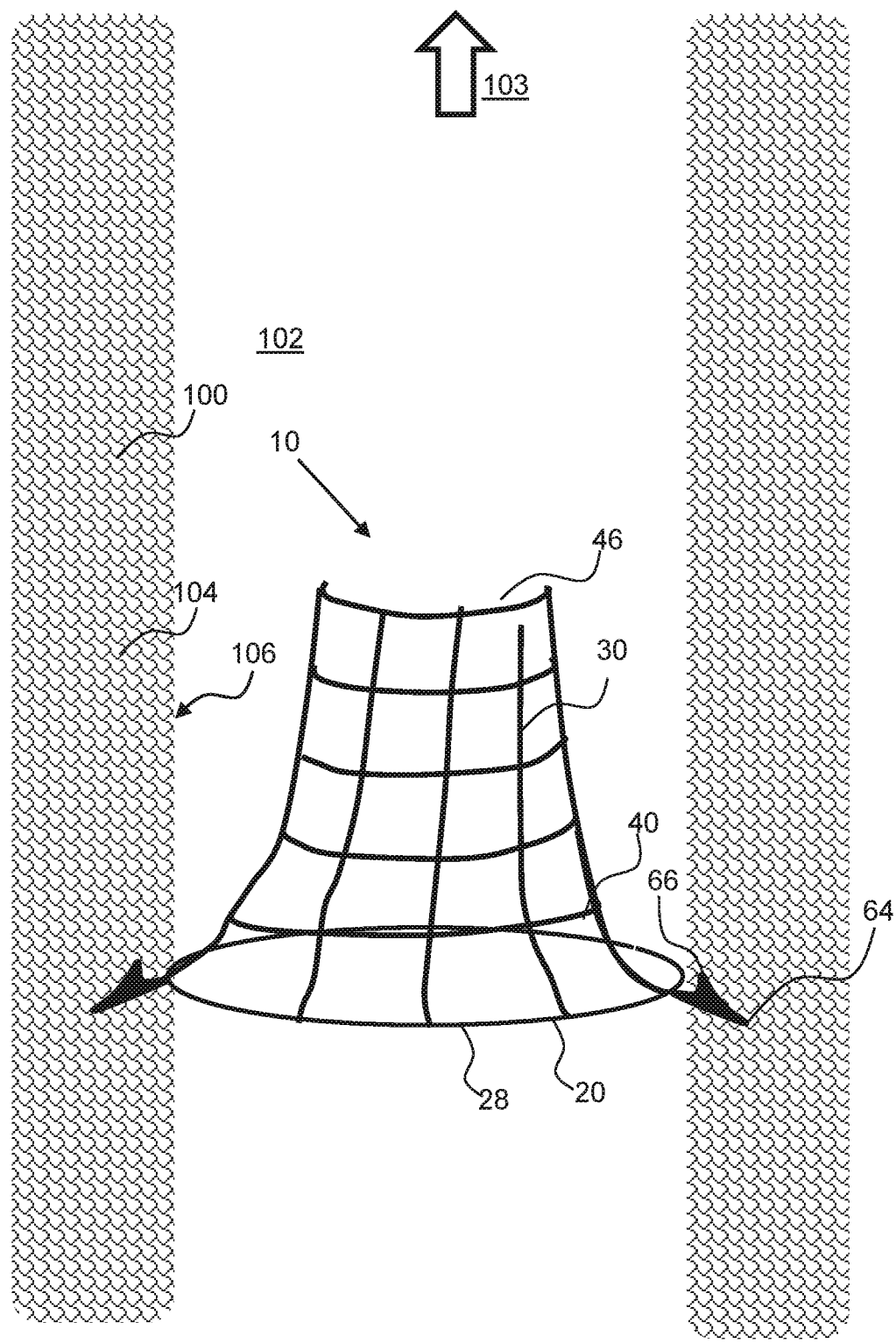
Figure 9:
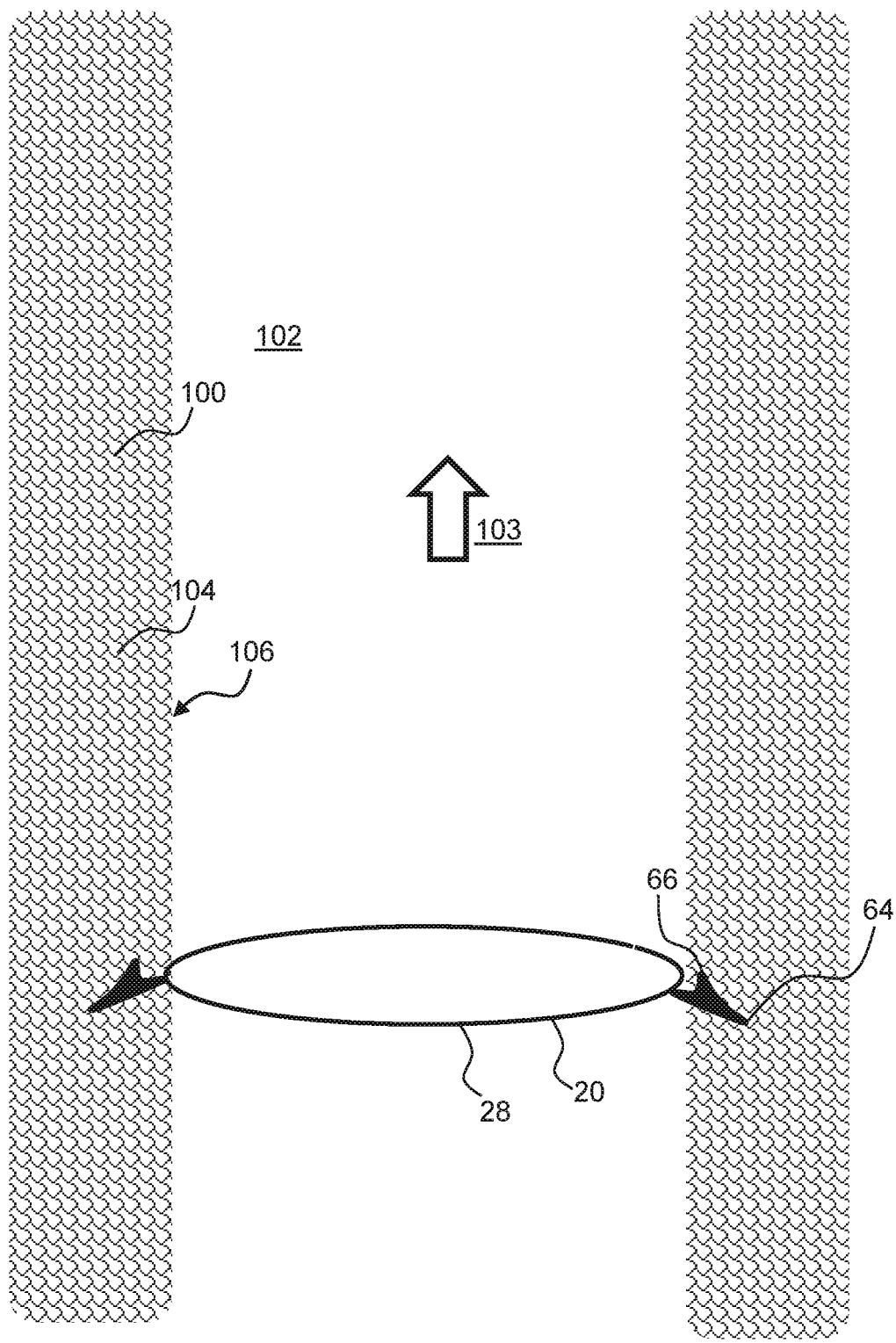
Figure 10:
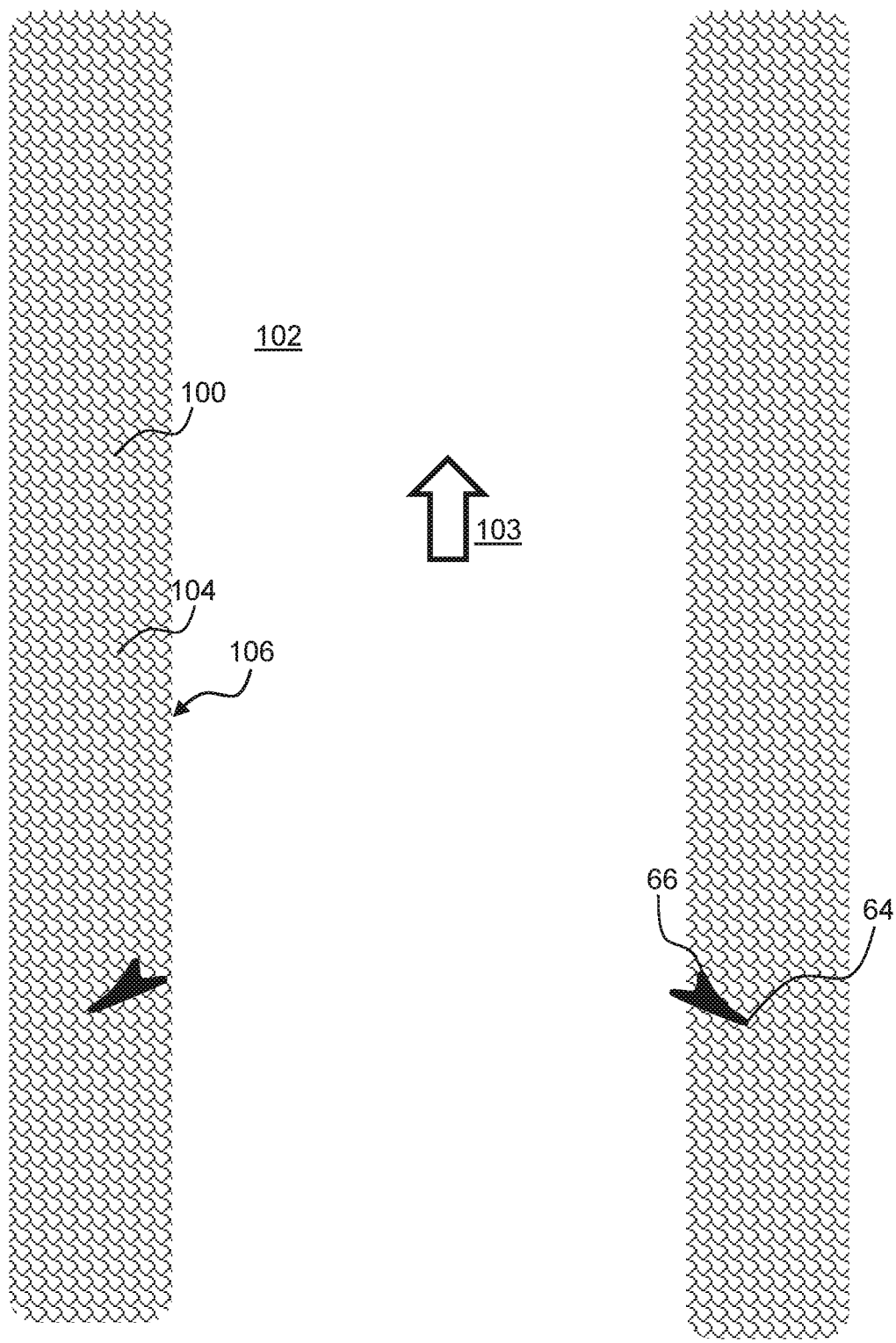

As shown in FIGS. 6 to 10, an exemplary vascular filter may be configured to progressively decompose over time. As shown in FIG. 6, every other ring strand 40 is dissolved leaving larger filter openings 46. As shown in FIG. 7, every other fill strand 30 is dissolved leaving even larger filter openings 46. As shown in FIG. 8, the distal end of the vascular filter dissolves before the proximal end. As shown in FIG. 9, the vascular filter portion has dissolved leaving the attachment ring 20 and the attachment barbs 60. As shown in FIG. 10, only the attachment barbs 60 are left retained in the vessel wall 104.

Figure 11:
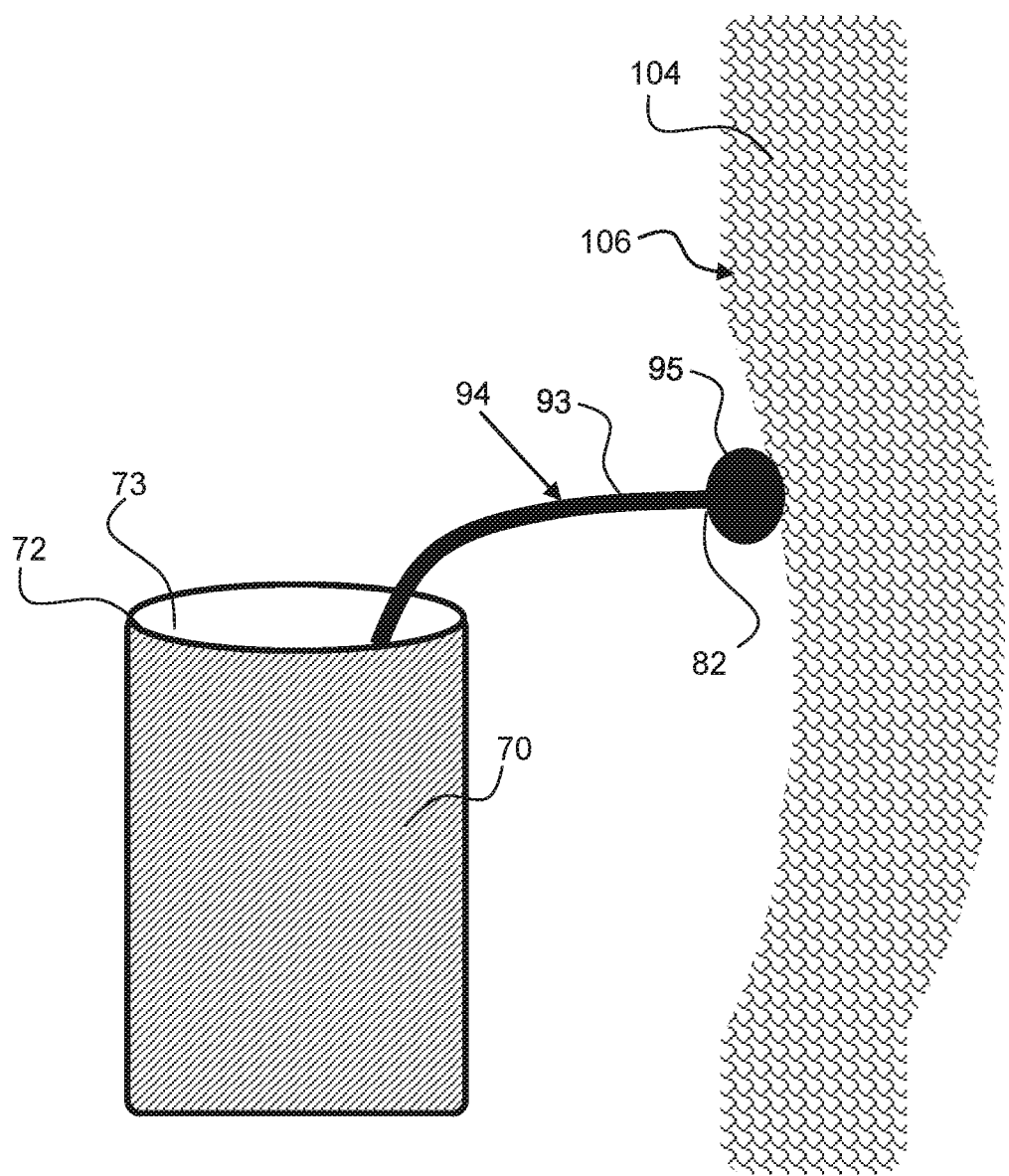
FIG. 11 shows a perspective view of a vessel distension device comprising a plurality of tensors having a distention end for pressing against the inside vessel wall.
Figure 12:
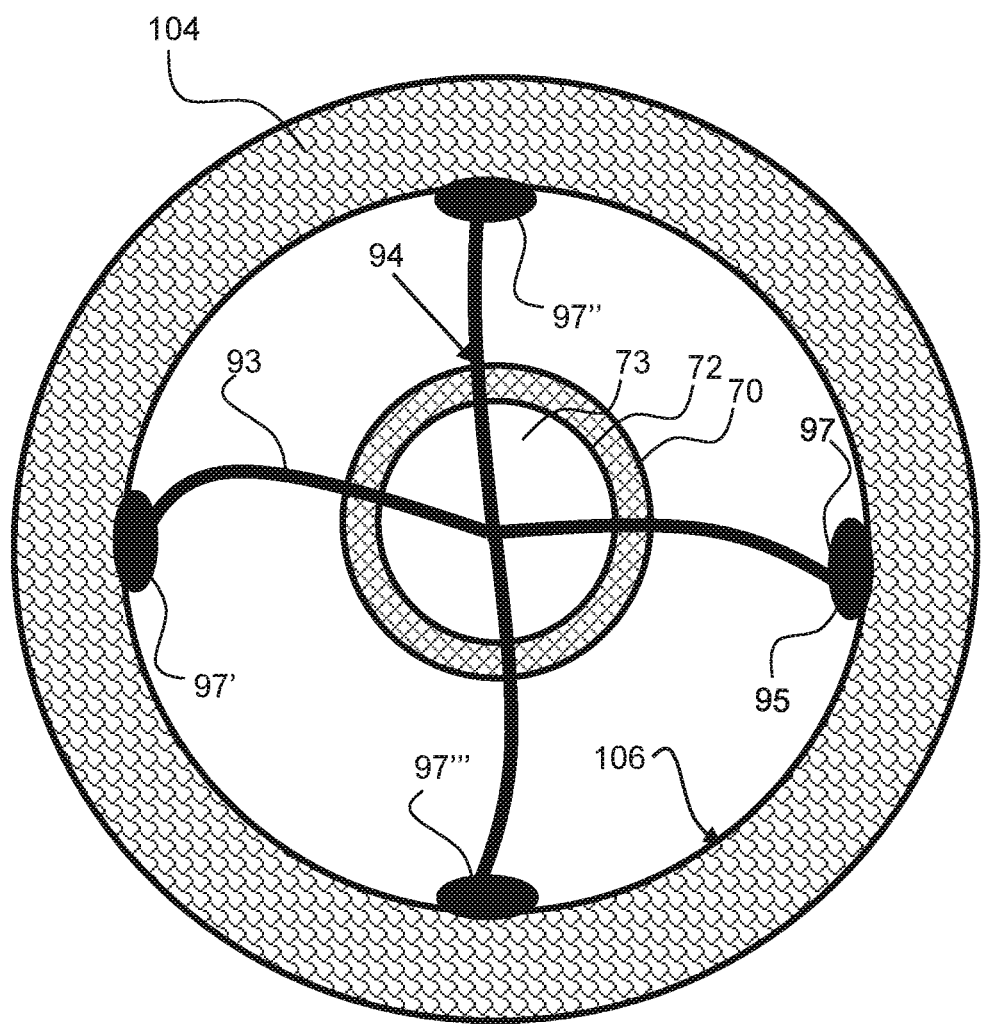
FIG. 12 shows a top view of a vessel distension device comprising a plurality of tensors pressing the vessel outward.

Referring now to FIGS. 11 and 12, a vessel distention device 94 comprises one or more distention tensors 93 having a distention end 95 with a distention feature 97 thereon, such as a blunt end for applying pressure to the inside vessel wall 106. As shown in FIG. 12, four distention tensors 93 extend from distal end opening 73 of the sheath 70 and extend radially outward to the inside vessel wall 106. The four distention tensors are circumferentially spaced at about 90 degrees, creating a substantially uniform spacing about the interior circumference of the vessel. Each of the distention ends 95 has a distention feature 97-97''' attached thereto, such as a blunt tip or pad or disc, that is pressed outward against the inside vessel wall to distend the vessel wall, as shown best in FIG. 11. The distention feature shown is disc having a diameter, or blunt dimension, a dimension measure across the extended end, that is at least five times greater than the diameter of the distension tensor 93. A vessel distention device may comprise one or more tensors with a distention feature coupled to the distention end. In an exemplary embodiment, a vessel distention device comprises three or more distention tensors.

Figure 13:
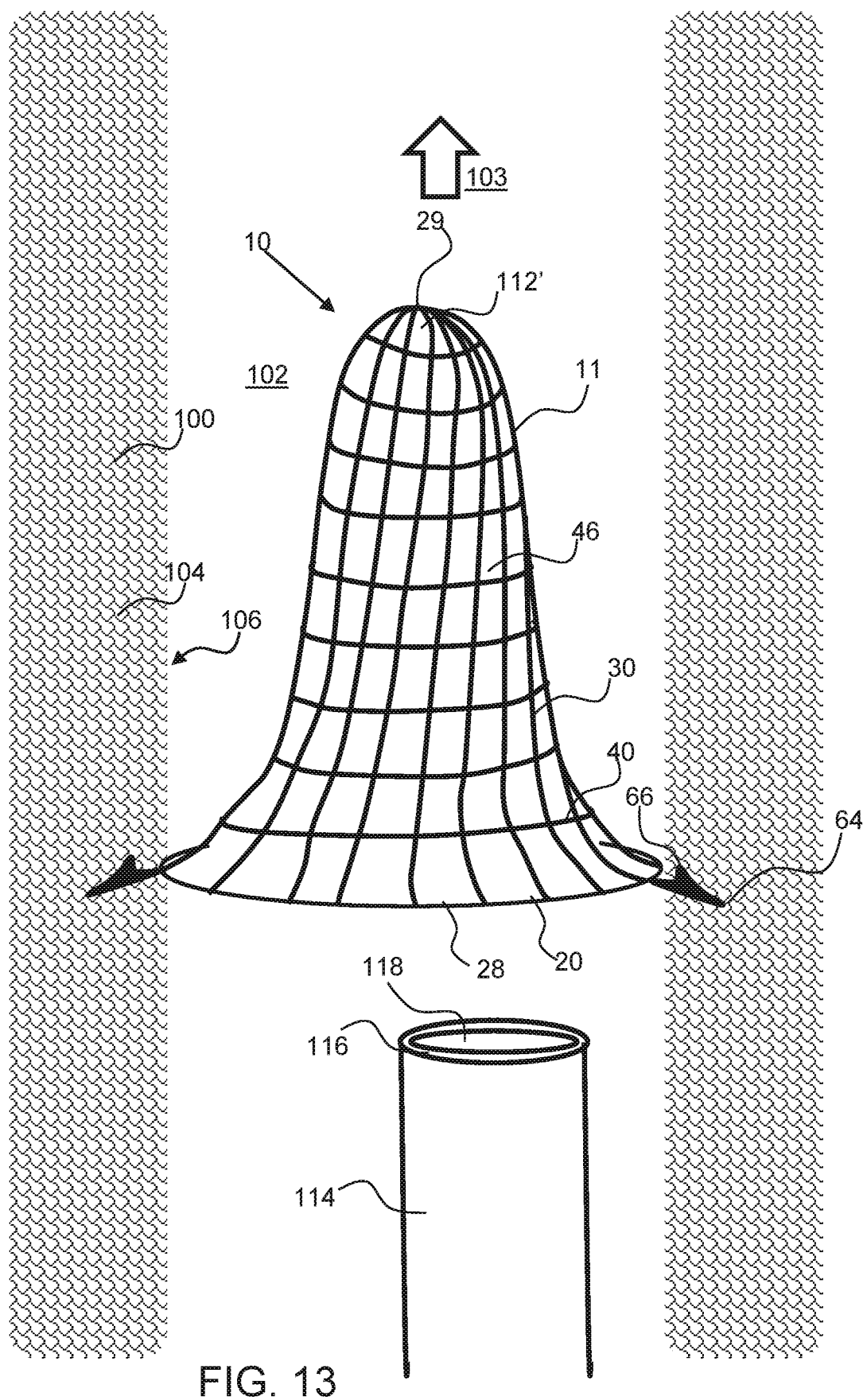
FIGS. 13 to 20 show an exemplary vascular filter retrieval system and method of using said system to retrieve a vascular filter.
Figure 14:
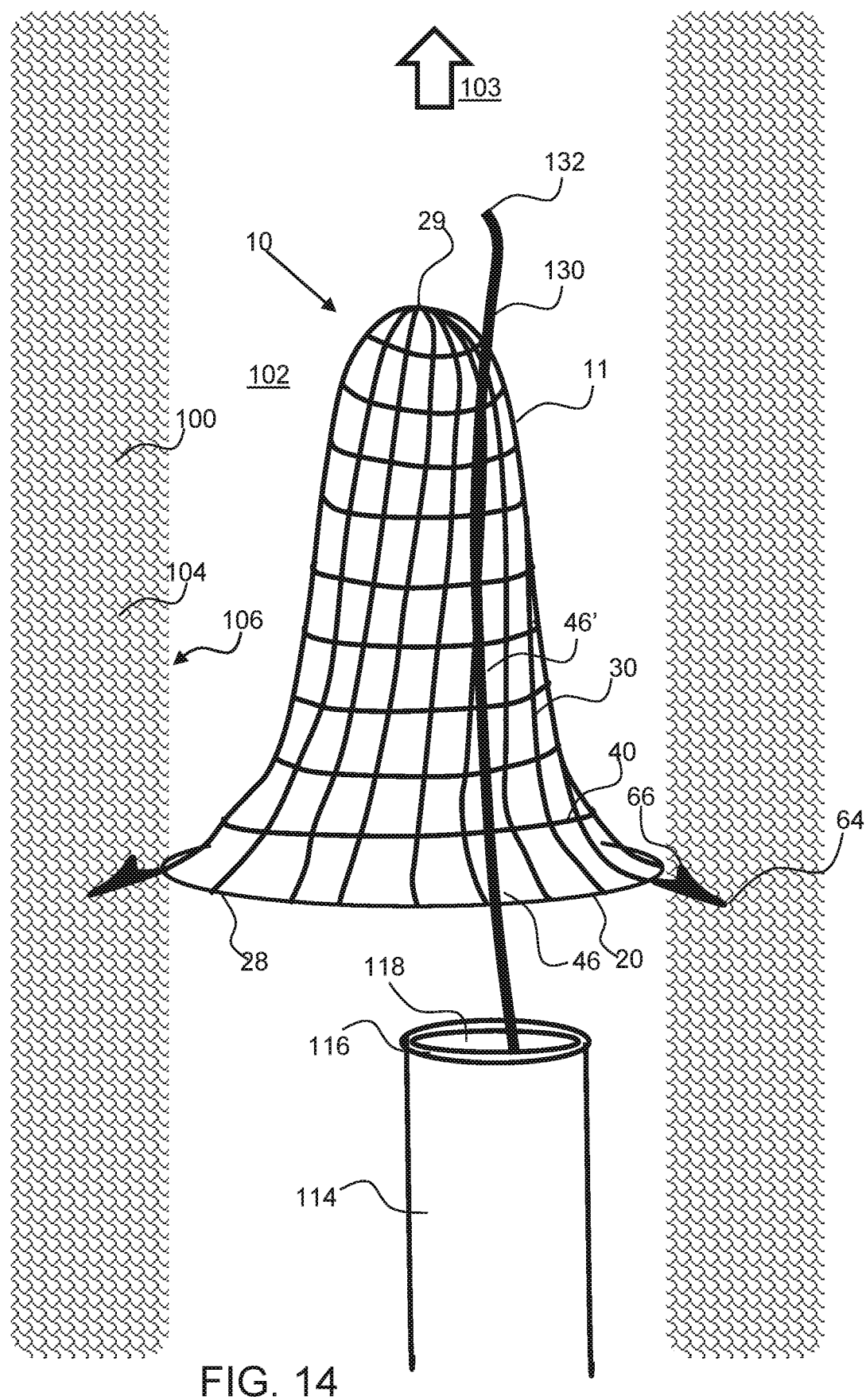
Figure 15:
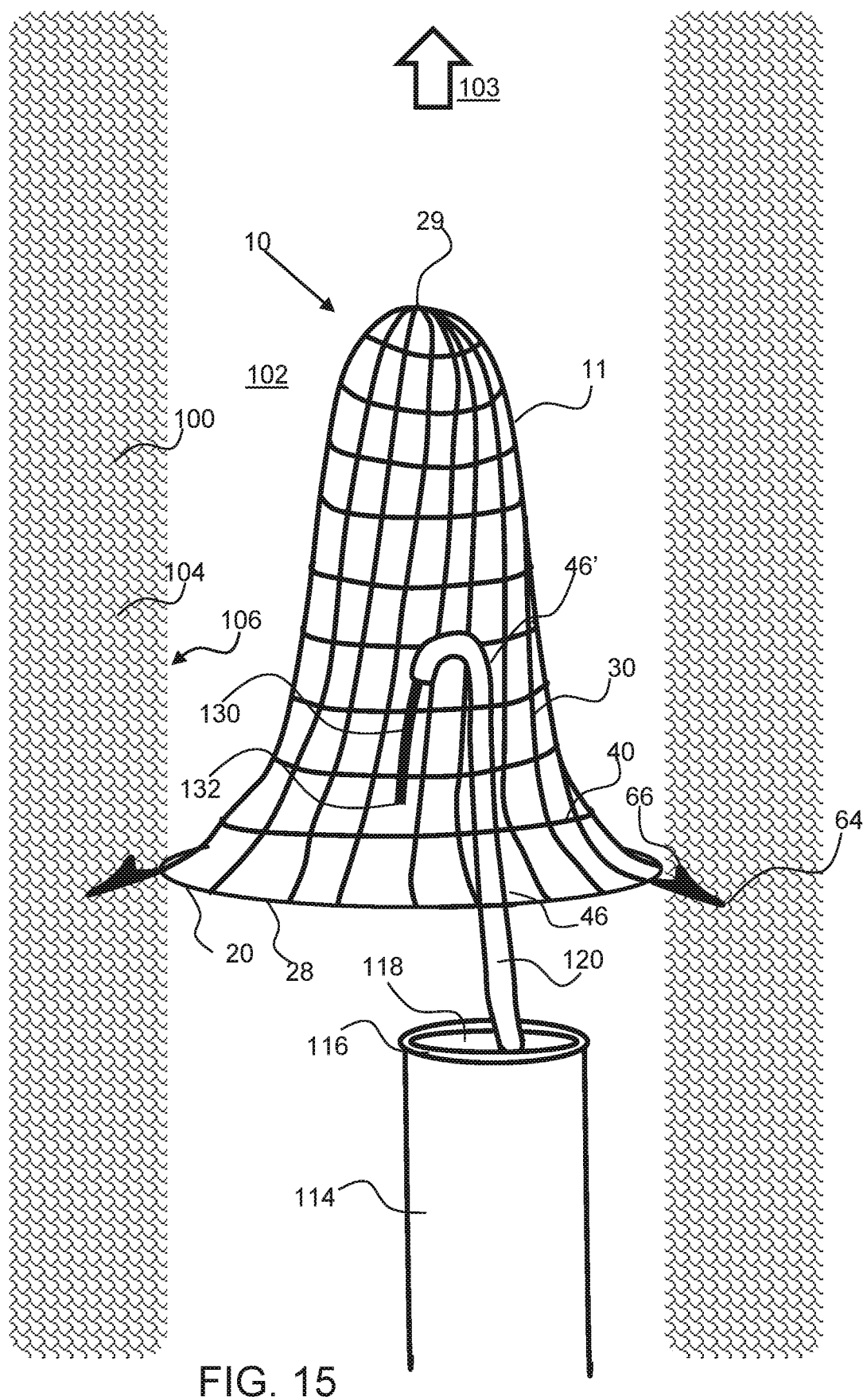
Figure 16:
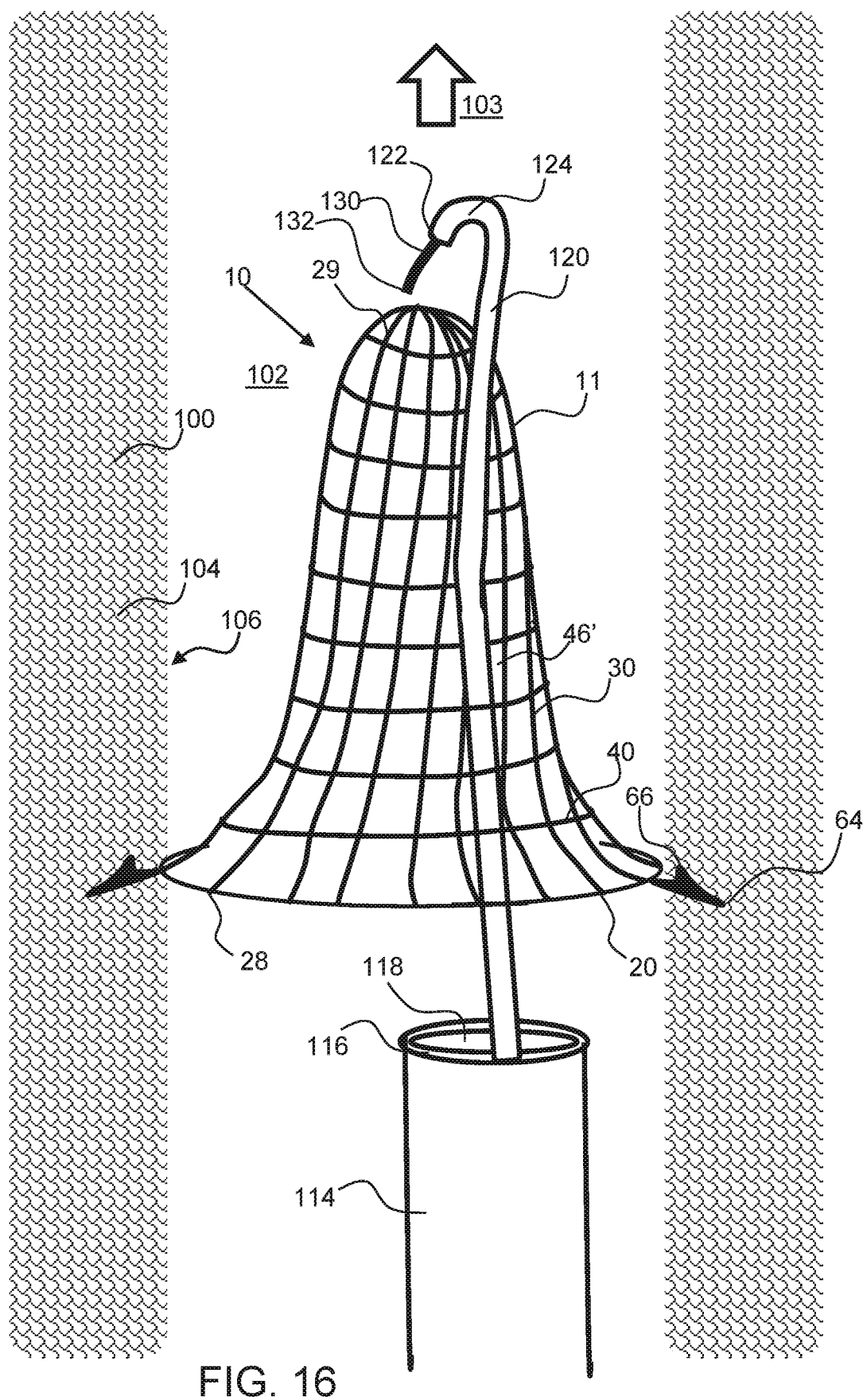
Figure 17:
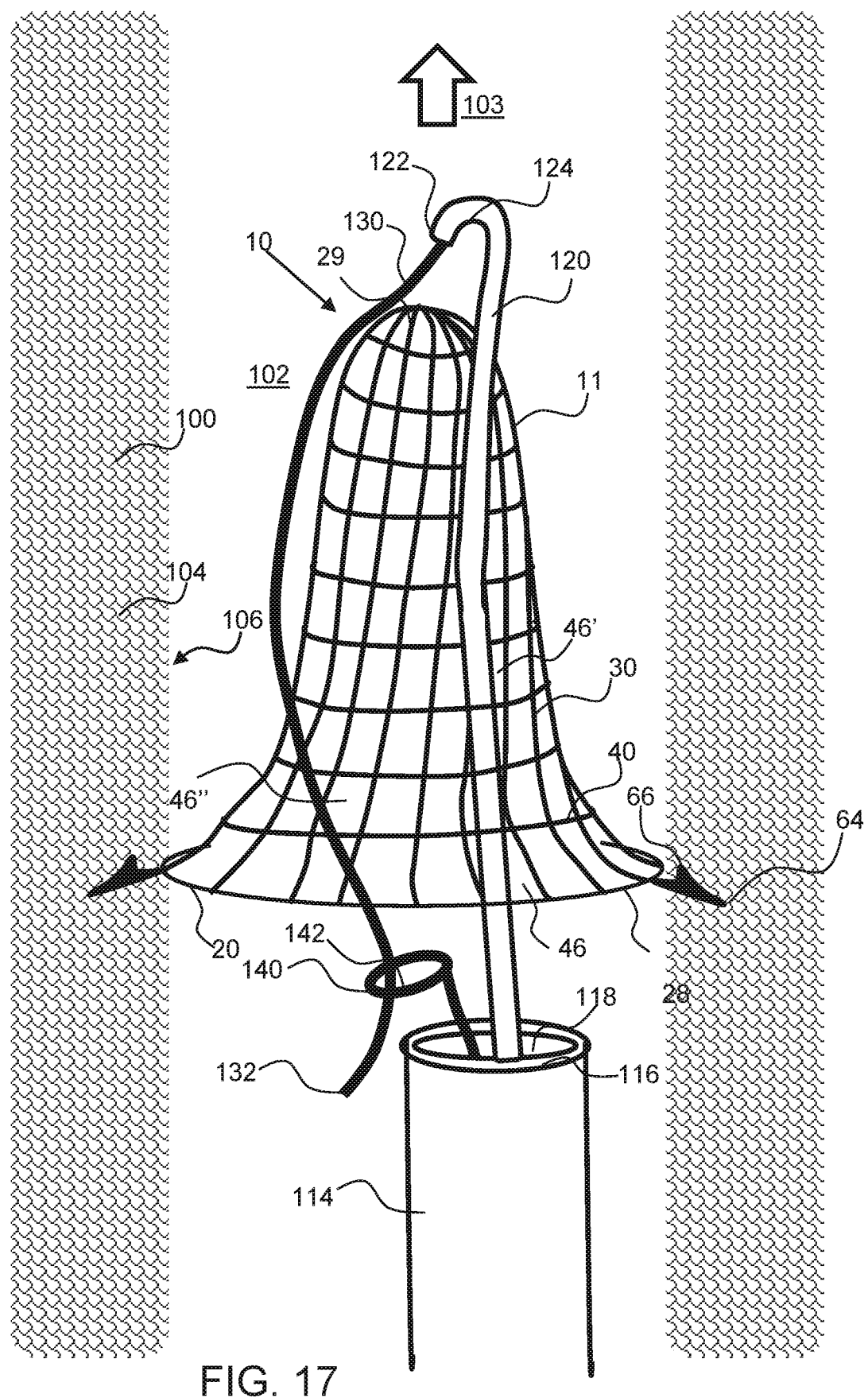
Figure 18:
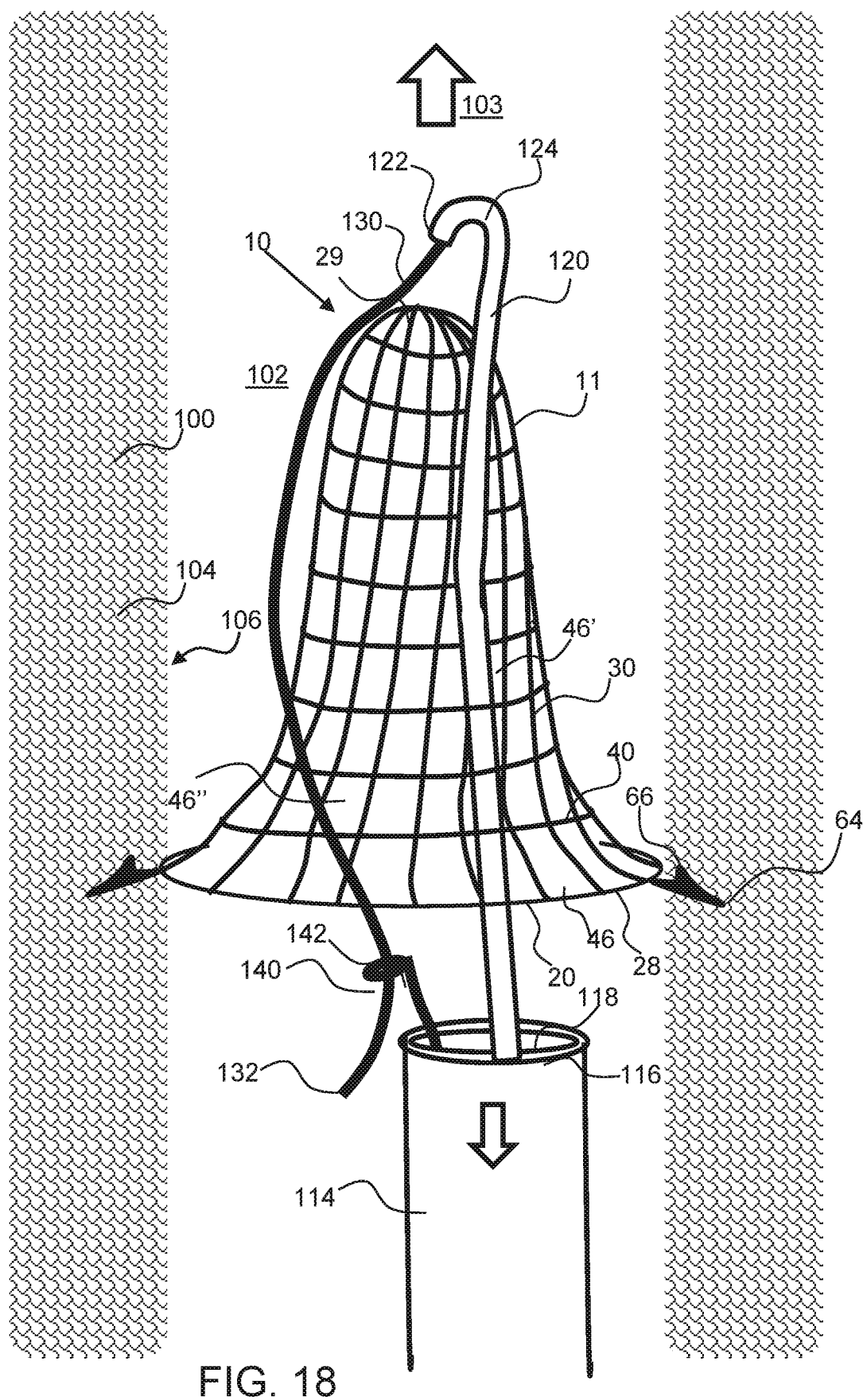
Figure 19:
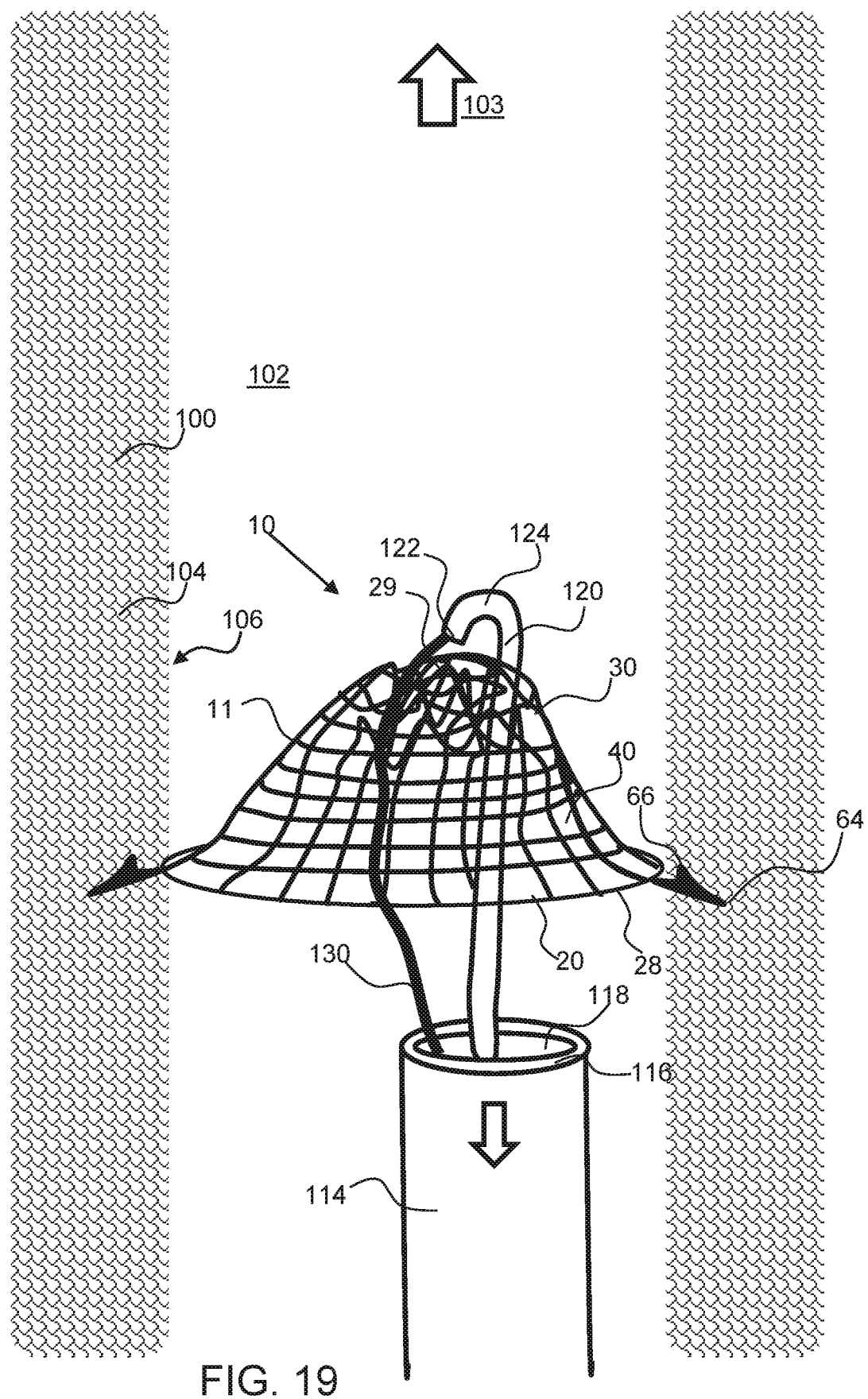
Figure 20:
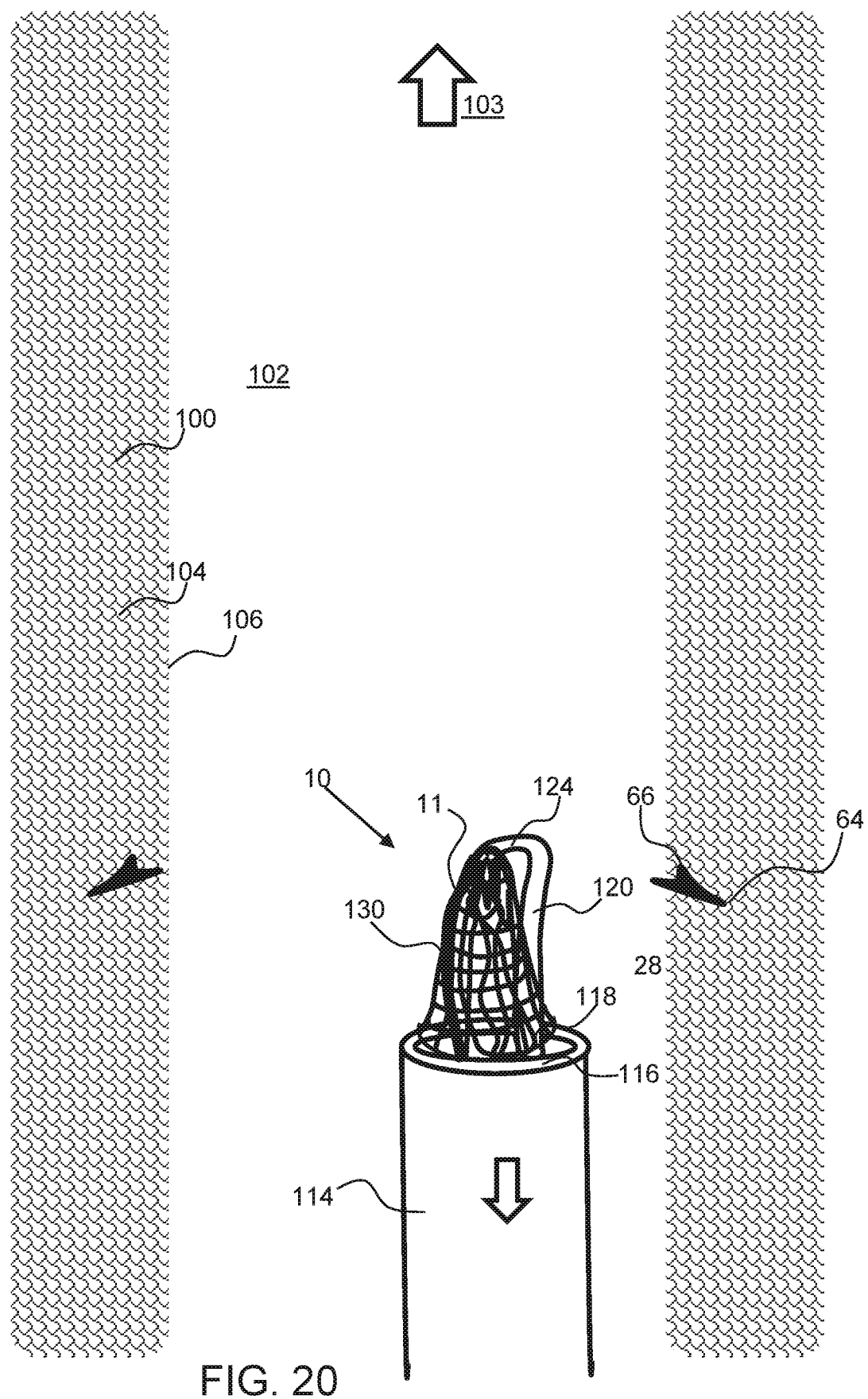

Referring now to FIGS. 13 to 20, an exemplary vascular filter retrieval system comprises a sheath for the introduction of a guidewire, a reverse curve catheter over the catheter, and an intravascular snare. As shown in FIG. 13, the sheath 114 is introduced into the vessel lumen 102 and located proximal to the vascular filter 10. The sheath has a distal end 116 having an opening 118 that is located on the proximal end 28 of the vascular filter 10. As shown in FIG. 14, a guidewire 130 is moved through the sheath and out of the sheath opening 118. The guidewire extends through filter opening 46' of the filter web 14. The distal end of the guidewire 132 is positioned distal the vascular filter 10. As shown in FIG. 15, a reverse curve catheter 120 is moved over the guidewire and out of the sheath opening 118. The guidewire also extends through filter opening 46'. As shown in FIG. 16, the distal end 122 of the reverse curve catheter 120 is positioned distal the distal end 29 of the vascular filter 10. The reverse curve portion 124 of the reverse curve catheter is distal the proximal end 28 of the vascular filter 10 and distal the attachment ring 20, such that the guidewire is directed back toward the distal end of the sheath. As shown in FIG. 17, the distal end 132 of the guidewire 130 has been advanced back toward the sheath 114 and is moved through filter opening 46" and into the snare opening 142 of the intravascular snare 140. The snare is then synched down, as shown in FIG. 18, to retain the guidewire in the snare. The reverse curve catheter and guidewire form a noose or loop around a portion of the vascular filter 10 and extends through one or more of the filter openings. The reverse curve catheter 120 and guidewire can then be pulled toward the sheath 114 and pulled into the sheath opening 118, as shown in FIGS. 19 and 20. The reverse curve catheter, guidewire and vascular filter can all be pulled into, or at least partially into the sheath and then pulled from the lumen and out of the body.

Figure 21:
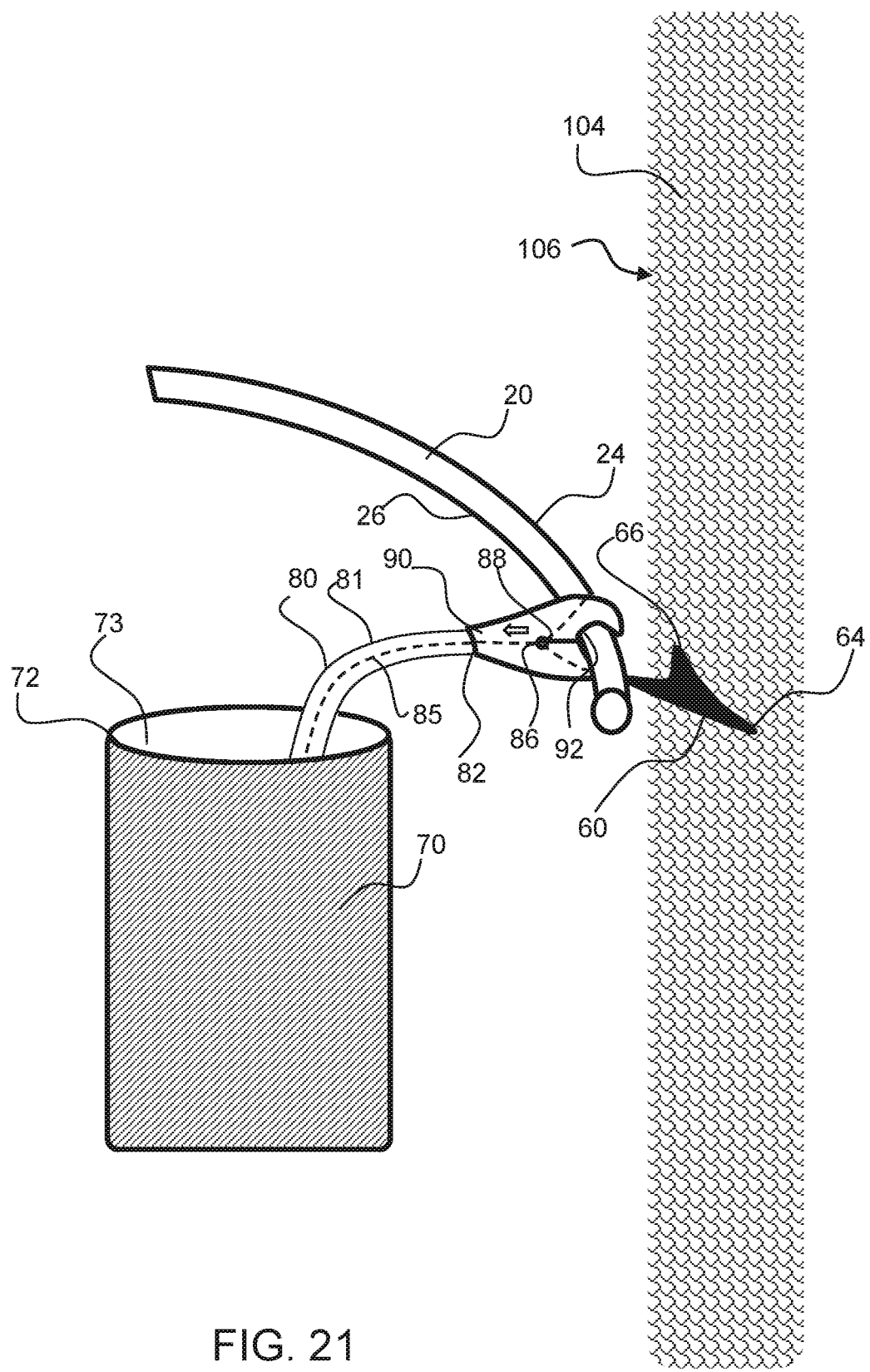
FIGS. 21 and 22 show an exemplary tensor having a stylet extending through a conduit of the tensor and connected to a release feature coupled to the tensor coupler.
Figure 22:
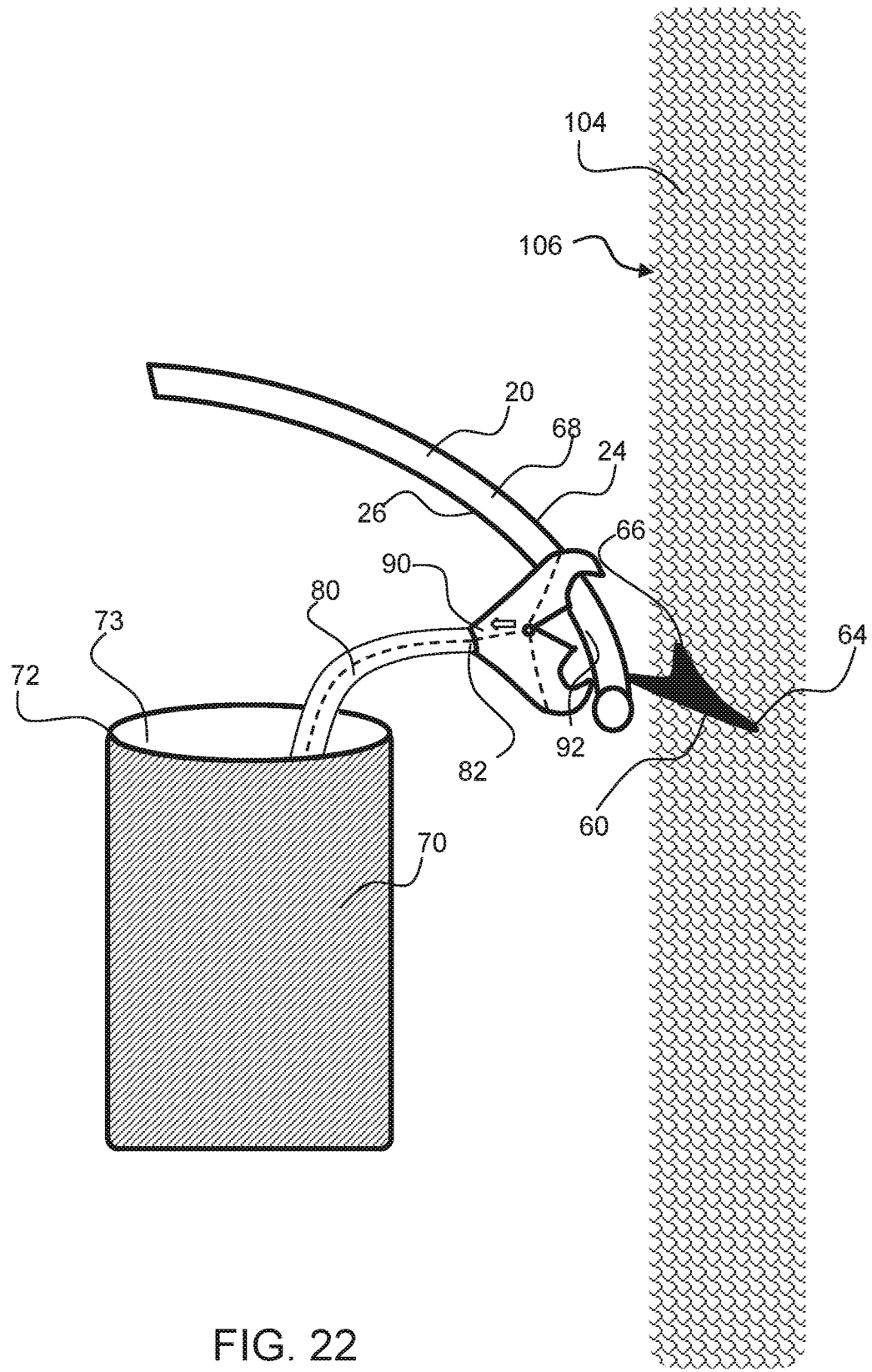

Referring now to FIGS. 21 and 22, an exemplary tensor 80 has a stylet 85 extending through a tensor conduit 81 of the tensor and is connected to a release feature 88 coupled to the tensor coupler 90. In FIG. 21 the tensor coupler is configured around the attachment ring 20, and in FIG. 22 the stylet has been pulled to release the tensor coupler from the attachment ring. The release feature may comprise a hinge 89 to allow the coupler slot 92 of the tensor coupler to be opened and released from the attachment ring. This hinge may be a living hinge that allows the tensor coupler to open. The connected end 86 of the stylet 85 may pull on the tensor coupler to open the coupler slot and enable release of the tensor coupler.

Figure 23:
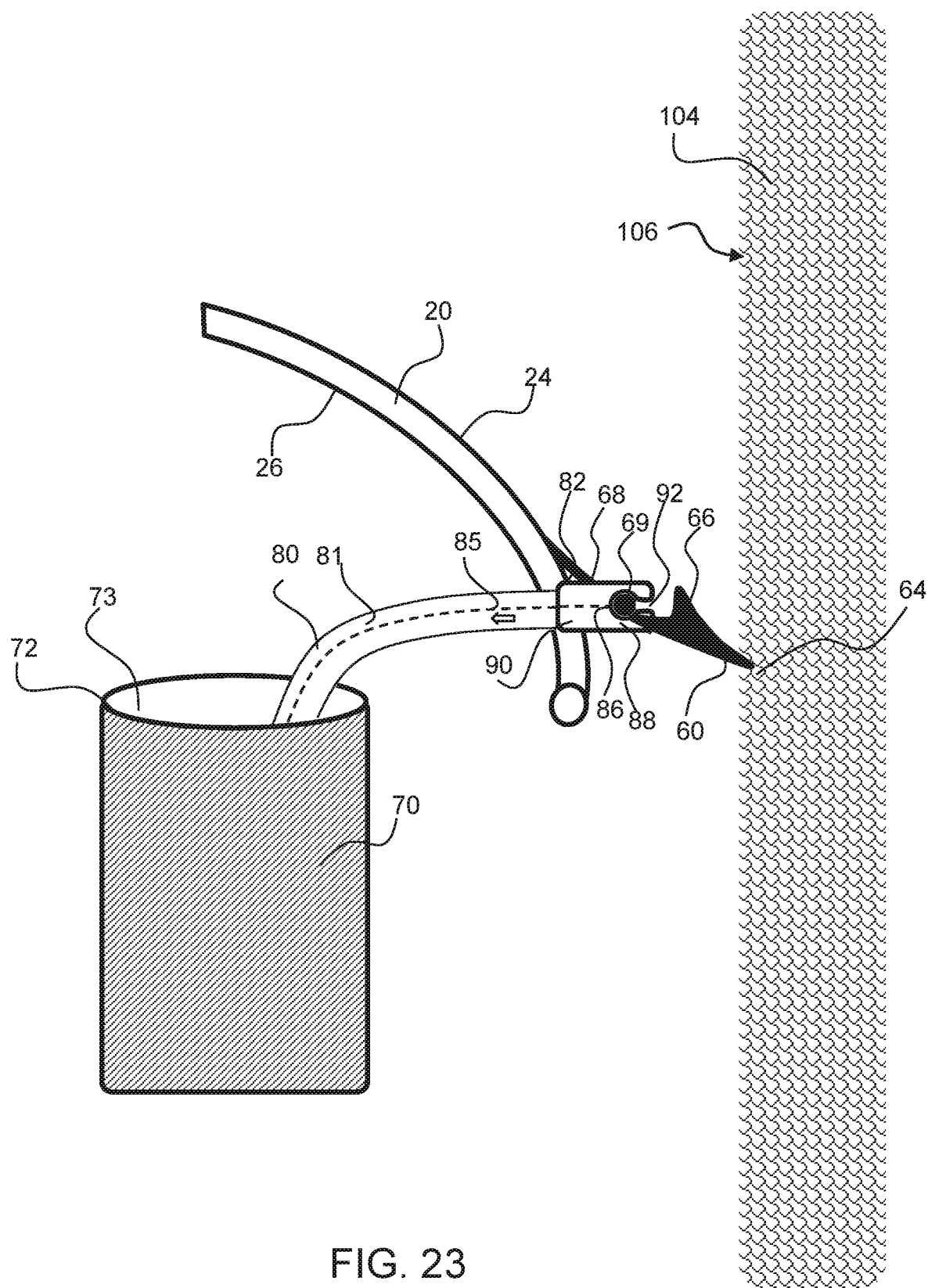
FIGS. 23 and 24 show an exemplary tensor having a stylet extending through a conduit of the tensor and connected to a release feature coupled the tensor coupler.
Figure 24:
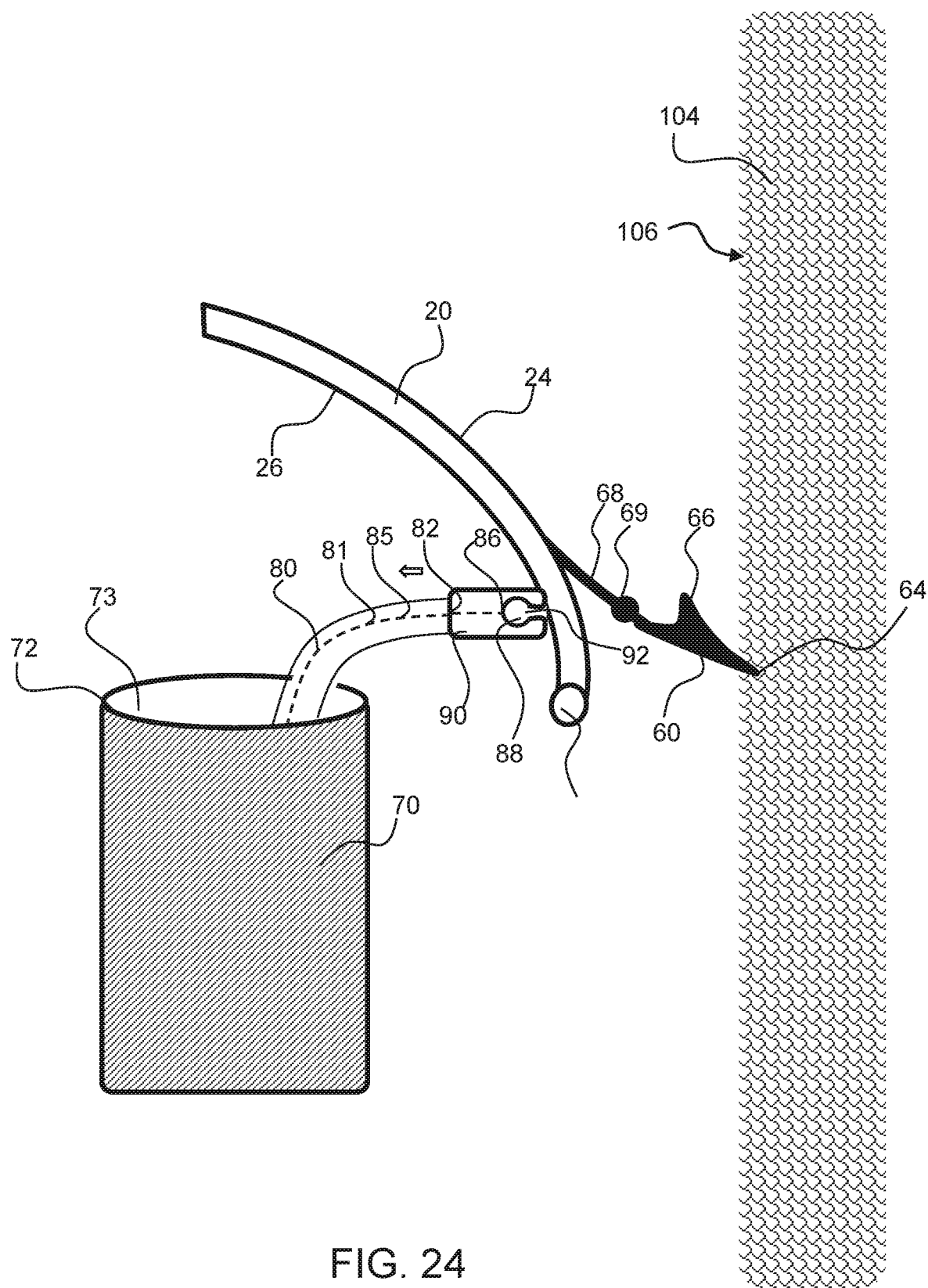

Referring now to FIGS. 23 and 24, an exemplary tensor 80 has a stylet 85 extending through a tensor conduit 81 of the tensor 80 and is connected to a release feature 88 coupled to the tensor coupler 90. The tensor coupler is coupled to a barb tether 68 that extends from the attachment ring 20 to the barb 60. Note that the barb tether may form or be part of the attachment ring, wherein the barb release feature is configured on the attachment ring and wherein the tensor coupler, on the extended end of the tensor, is detachably attached with the barb release feature. A barb release feature may be geometry configured to be retained by the tensor coupler, such as having a round cross-section that fits into a circular recess in the tensor coupler, or vice versa. In FIG. 23 the tensor coupler 90 is coupled to a barb tether 68, and in FIG. 24 the stylet 85 has been pulled to release the tensor coupler from the barb tether. The tensor coupler has a slot and an aperture to receive a barb release feature 69, a protrusion of the barb tether, such as a bead. Pulling the stylet opens the slot to allow the barb release feature to be slid out of the narrow slot, narrower in dimension than the aperture in the tensor coupler.

Figure 25:
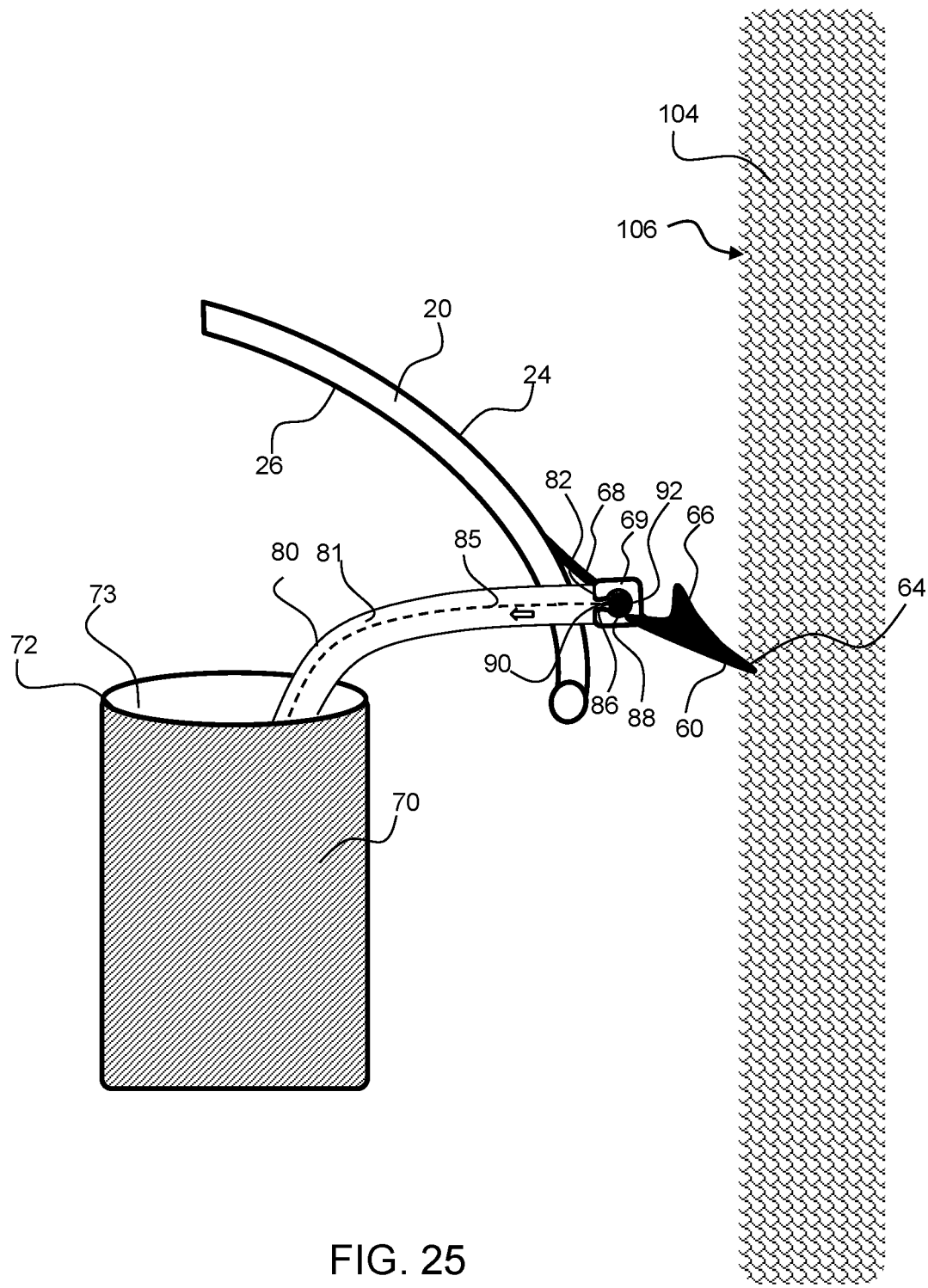
FIGS. 25 and 26 show an exemplary tensor having a stylet extending through a conduit of the tensor and connected to a release feature coupled the tensor coupler.
Figure 26:
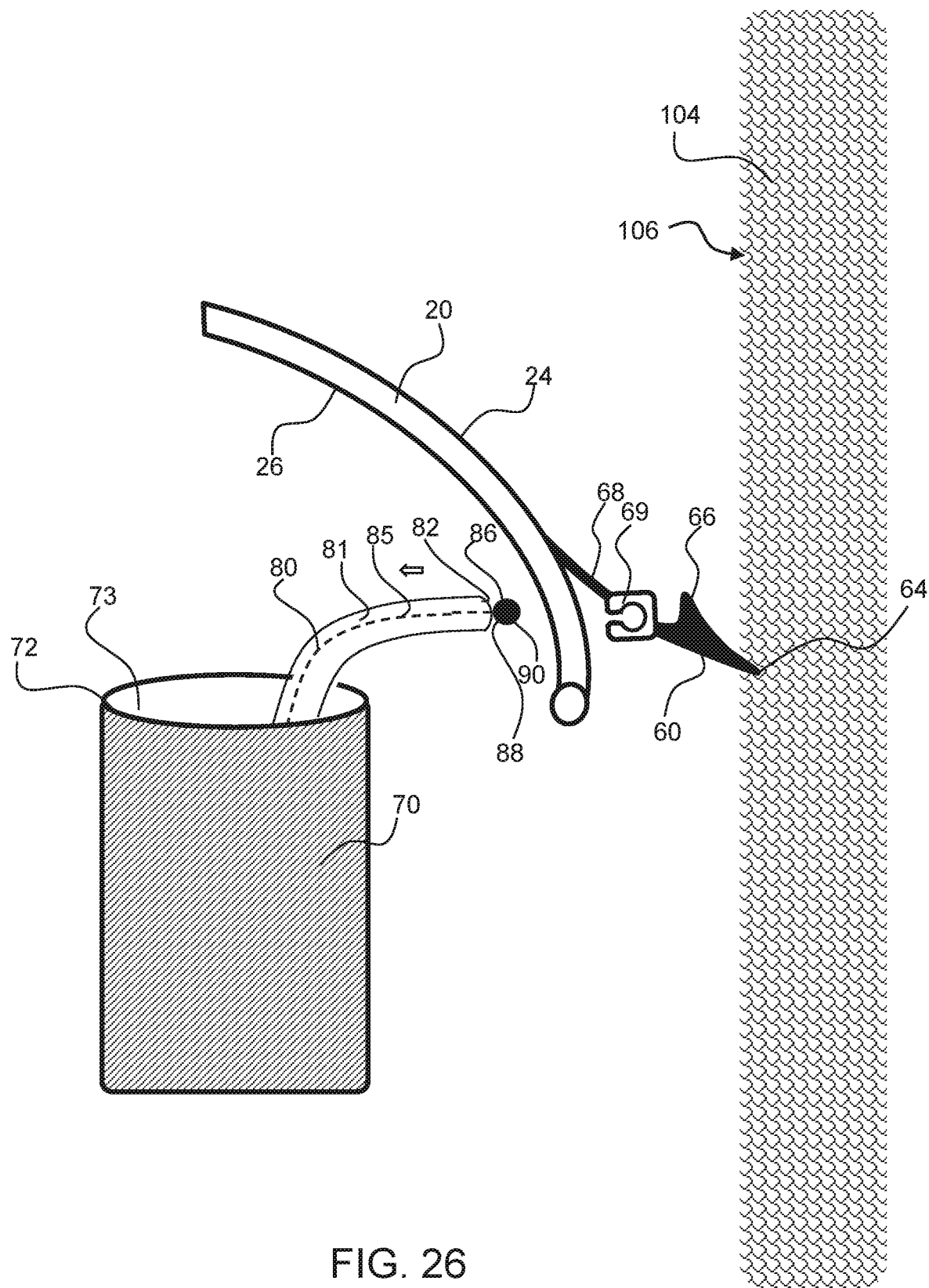

Referring now to FIGS. 25 and 26, an exemplary tensor 80 has a stylet 85 extending through a tensor conduit 81 of the tensor 80 and connected to a release feature 88 coupled the tensor coupler 90. The tensor coupler is coupled to a barb tether 68 that extends from the attachment ring 20 to the barb 60. In FIG. 25 the tensor coupler 90 is coupled to a barb tether 68, and in FIG. 26 the stylet 85 has been pulled to release the tensor coupler from the barb tether. The tensor coupler is a protrusion, or enlargement of the stylet, such as a spherical bead, that is retained in the barb release feature 69, which is a slot having a curved aperture to receive the stylet release feature 88. Pulling the stylet opens the slot of the barb release feature 69 to allow the stylet release feature to be slid out of the narrow slot, narrower in dimension than the aperture in the barb release feature 69. As shown in FIG. 26, the bead on the connected end 86 of the stylet is released from the barb release feature 69.

Figure 27:
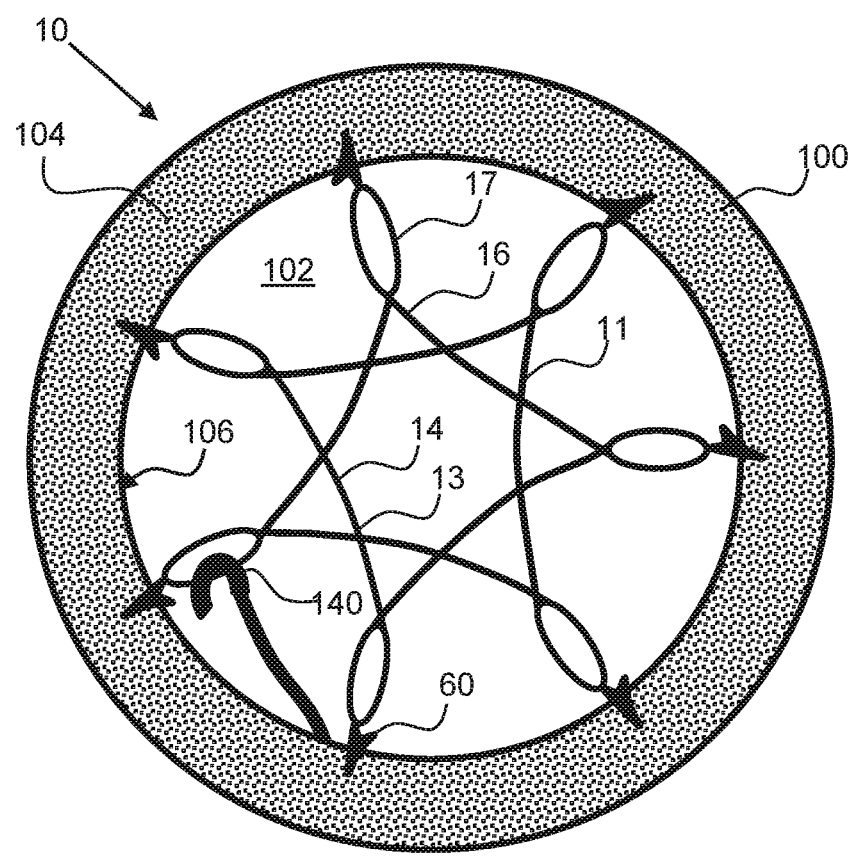
FIG. 27 shows a top view of vessel having a filter web retained to the inside of the vessel wall by attachment barbs.

As shown in FIG. 27, a filter web 14 is retained to the inside of the vessel wall 106 by attachment barbs 60. The filter portion 11 in this embodiment is a spirographic loop 16 made up of a single continuous filter strand 13 configured with filter end loops 17 with the attachment barbs connected thereto. This type of filter web may enable an intravascular snare 140 to couple with and withdraw the filter web from a single location, as the filter web is made of a continuous looped strand.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A vascular filter system comprising:
   a) a vascular filter comprising:
      i) a barb tether having a barb release feature;
      ii) a plurality of attachment barbs coupled to the barb tether;
      iii) a filter web comprising a filter strand forming filter openings,
         wherein a filter web portion is coupled to the barb tether;
   b) a deployment sheath having a distal end opening;
   c) a plurality of tensors, each of said plurality of tensors comprising:
      i) an extended end;
      ii) a tensor coupler attached to said extended end;
         wherein the plurality of tensors are retained within the deployment sheath;
         wherein the plurality of tensor couplers are coupled with the barb release feature;
         wherein each of the tensor couplers is detachably attached to the barb release feature; and
         wherein the plurality of tensors are shape memory material and wherein each is configured to extend radially outward from the distal end opening of the deployment sheath to press the barb tether, and the attachment barbs coupled thereto, against a vessel wall;
   d) a plurality of stylets, wherein each of the stylets extending along each of the tensors to each of the tensor couplers and configured to release each of the tensor couplers from the barb tether.

2. The vascular filter system of claim 1, wherein the barb tether forms an attachment ring.

3. The vascular filter system of claim 1, wherein each of the tensor couplers extends at least partially around the barb release feature and wherein each of the stylets is configured to open each of the tensor couplers when tension is applied to release each of the tensor couplers from the barb release feature.

4. The vascular filter system of claim 3, wherein the barb release feature comprises a shape of the barb tether configured to fit within each of the tensor couplers.

5. The vascular filter system of claim 4, wherein the barb tether is a portion of an attachment ring.

6. The vascular filter system of claim 4, wherein the barb tether extends from an attachment ring.

7. The vascular filter system of claim 1, wherein the barb release feature extends at least partially around each of the tensor couplers and wherein the stylet is configured to pull each of the tensor couplers from the barb release feature when tension is applied to release each of the tensor couplers from the barb release feature.

8. The vascular filter system of claim 1, wherein the filter web comprises a bioresorbable filter strand.

9. The vascular filter system of claim 1 wherein the filter web consists essentially of a bioresorbable filter strand.

10. The vascular filter system of claim 1, wherein the filter openings have a dimension of no more than 10 mm.

11. The vascular filter system of claim 1, wherein the plurality of attachment barbs are metallic.

12. The vascular filter system of claim 1, wherein the filter web consists essentially of a bioresorbable filter strand, and wherein the plurality of attachment barbs are metallic.

13. The vascular filter system of claim 1, wherein each of the plurality of attachment barbs comprises an insert end and a barb portion.

14. The vascular filter system of claim 1, comprising a radiopaque material on an attachment ring.

15. The vascular filter system of claim 1, comprising a radiopaque material on one or more of the attachment barbs.

16. The vascular filter system of claim 1, comprising a radiopaque material on the filter web.

17. The vascular filter system of claim 1, wherein the filter web comprises a first portion of a plurality of filter strands having a higher dissolving rate than a second portion of a plurality of filter strands.

18. A vascular filter system comprising:
   a) a vascular filter comprising:
      i) a barb tether having a barb release feature;
      ii) a plurality of attachment barbs coupled to the barb tether;
      iii) a filter web comprising a filter strand forming filter openings,
         wherein a filter web portion is coupled to the barb tether;
   b) a deployment sheath having a distal end opening;
   c) a plurality of tensors, each of said plurality of tensors comprising:
      i) an extended end;
      ii) a tensor coupler attached to said extended end;

wherein the plurality of tensors are retained within the deployment sheath;

wherein the plurality of tensor couplers are coupled with the barb release feature;

wherein each of the tensor couplers is detachably attached to the barb release feature; and wherein the plurality of tensors are shape memory material and wherein each are configured to extend radially outward from the distal end opening of the deployment sheath to press the barb tether, and the attachment barbs coupled thereto, against a vessel wall; and wherein the filter web consists of a spirographic loop.

19. The vascular filter system of claim 18, wherein the spirographic loop consists of a single continuous strand.

* * * * *